(12) United States Patent
Sakamoto et al.

(10) Patent No.: US 12,371,652 B2
(45) Date of Patent: Jul. 29, 2025

(54) PRIMING METHOD OF MICROPARTICLE SORTING MICROCHIP, MICROPARTICLE SORTING METHOD, MICROPARTICLE SORTING DEVICE, AND PROGRAM

(71) Applicant: Sony Group Corporation, Tokyo (JP)

(72) Inventors: Naohisa Sakamoto, Kanagawa (JP); Masahiro Matsumoto, Kanagawa (JP); Shinichi Kai, Tokyo (JP); Shinji Tashiro, Tokyo (JP); Kazuya Takahashi, Kanagawa (JP); Yoshifumi Machida, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 522 days.

(21) Appl. No.: 17/772,987

(22) PCT Filed: Aug. 27, 2020

(86) PCT No.: PCT/JP2020/032353
§ 371 (c)(1),
(2) Date: Apr. 28, 2022

(87) PCT Pub. No.: WO2021/090555
PCT Pub. Date: May 14, 2021

(65) Prior Publication Data
US 2023/0348840 A1    Nov. 2, 2023

(30) Foreign Application Priority Data
Nov. 5, 2019    (JP) .................................. 2019-200974

(51) Int. Cl.
*C12M 1/00*    (2006.01)
*C12M 1/26*    (2006.01)
*C12M 3/06*    (2006.01)

(52) U.S. Cl.
CPC ............ *C12M 47/04* (2013.01); *C12M 23/16* (2013.01); *C12M 33/12* (2013.01)

(58) Field of Classification Search
CPC ...... C12M 23/16; C12M 33/12; C12M 47/04; G01N 15/14; G01N 37/00
See application file for complete search history.

(56) References Cited

U.S. PATENT DOCUMENTS 7,842,240 B2 *   11/2010   Yamamoto ............ B01L 3/5027
                                                              422/403
2005/0255000 A1    11/2005   Yamamoto et al.
(Continued)

FOREIGN PATENT DOCUMENTS

EP        3 633 347 A1     4/2020
JP       2005-345463 A    12/2005
(Continued)

OTHER PUBLICATIONS

International Search Report with English Translation thereof mailed Nov. 10, 2020 in connection with International Application No. PCT/JP2020/032353.

*Primary Examiner* — Jennifer Wecker
(74) *Attorney, Agent, or Firm* — Wolf, Greenfield & Sacks, P.C.

(57) ABSTRACT

To provide a method of efficiently performing priming on a microparticle sorting microchip.
The present technology provides a priming method of a microparticle sorting microchip provided with a sample liquid flow path, a sheath liquid flow path that joins the sample liquid flow path at a junction, a joined flow path including the junction at one end, a microparticle recovery flow path connected to the joined flow path via a connection flow path at the other end of the joined flow path, a branching flow path connected to the joined flow path at the other end of the joined flow path, and an introduction flow (Continued)

path configured to introduce a liquid into the connection flow path, the method provided with a first priming step of supplying a first liquid from the introduction flow path to the connection flow path, and performing priming on the microparticle recovery flow path by the first liquid, and a second priming step of allowing a second liquid to flow from the sheath liquid flow path to the joined flow path, and performing priming on the branching flow path by the second liquid.

15 Claims, 9 Drawing Sheets

(56) References Cited

U.S. PATENT DOCUMENTS

| | | | |
|---|---|---|---|
| 2008/0261295 A1* | 10/2008 | Butler | C12M 47/04 |
| | | | 436/53 |
| 2014/0048458 A1 | 2/2014 | Ito | |
| 2015/0114093 A1 | 4/2015 | Appleyard et al. | |
| 2018/0163713 A1 | 6/2018 | Morachis et al. | |
| 2019/0339189 A1 | 11/2019 | Takeda et al. | |

FOREIGN PATENT DOCUMENTS

| | | |
|---|---|---|
| JP | 2012-127922 A | 7/2012 |
| JP | 2014-036604 A | 2/2014 |
| JP | 2017-504037 A | 2/2017 |
| JP | 2018-523114 A | 8/2018 |
| WO | WO 2018/052137 A1 | 3/2018 |
| WO | WO 2018/216279 A1 | 11/2018 |
| WO | WO 2019/098126 A1 | 5/2019 |

* cited by examiner

PRIMING METHOD OF MICROPARTICLE SORTING MICROCHIP, MICROPARTICLE SORTING METHOD, MICROPARTICLE SORTING DEVICE, AND PROGRAM

CROSS REFERENCE TO RELATED APPLICATIONS

This is a U.S. National Stage Application under 35 U.S.C. § 371, based on International Application No. PCT/JP2020/032353, filed Aug. 27, 2020, which claims priority to Japanese Patent Application JP 2019-200974, filed Nov. 5, 2019, each of which is hereby incorporated by reference in its entirety.

TECHNICAL FIELD

The present technology relates to a priming method of a microparticle sorting microchip, a microparticle sorting method, a microparticle sorting device, and a program.

BACKGROUND ART

Various microparticle sorting devices have been developed so far to sort a microparticle. For example, in a particle sorting system used in a flow cytometer, a laminar flow including a sample liquid including cells and a sheath liquid is discharged from an orifice formed in a flow cell or a microchip. When being discharged, predetermined vibration is applied to the laminar flow to form a droplet. A moving direction of the formed droplet is electrically controlled depending on whether or not this includes a target particle, so that the target particle is sorted.

A technology of sorting the target particle within the microchip without forming the droplet in the above-described manner is also developed. For example, following Patent Document 1 discloses "A microchip comprising: a sample liquid introduction flow path through which a sample liquid including a microparticle flows; at least a pair of sheath liquid introduction flow paths that join the sample liquid introduction flow path from both sides to introduce a sheath liquid around the sample liquid; a joined flow path communicated with the sample liquid introduction flow path and the sheath liquid introduction flow path in which the liquids flowing through the flow paths join to flow; a negative pressure suction unit communicated with the joined flow path to suck to draw in a microparticle being a recovery target; and at least a pair of discharging flow paths provided on both sides of the negative pressure suction unit to be communicated with the joined flow path." (claim 1). In the microchip, the target particle is recovered into the negative pressure suction unit by suction.

CITATION LIST

Patent Document

Patent Document 1: Japanese Patent Application Laid-Open No. 2012-127922

SUMMARY OF THE INVENTION

Problems to be Solved by the Invention

In microparticle sorting in the microchip described above, the microparticle is recovered through a specific flow path. However, there is a case where the microparticle such as a cell, for example, is non-specifically adsorbed to a wall surface of the flow path. Furthermore, there also is a case where the microparticle is non-specifically adsorbed to an inner surface of a container into which this is recovered. Such adsorption is undesirable for cell activity and also for recovery efficiency of the microparticles.

In order to prevent such non-specific adsorption, it is conceivable to perform priming on the flow path through which the microparticle passes and the container into which the microparticle is recovered. However, for example, in a case where the microparticle is a cell, a liquid used for the priming may be required to include a relatively expensive component. Therefore, in such a case, it is desirable to perform the priming with a smaller amount of liquid.

On the basis of above, the present technology aims to provide an efficient priming method.

Solutions to Problems

The inventors found that the above-described problem may be solved by a specific method.

That is, the present technology provides a priming method of a microparticle sorting microchip provided with:
a sample liquid flow path;
a sheath liquid flow path that joins the sample liquid flow path at a junction;
a joined flow path including the junction at one end;
a microparticle recovery flow path connected to the joined flow path via a connection flow path at the other end of the joined flow path;
a branching flow path connected to the joined flow path at the other end of the joined flow path; and
an introduction flow path configured to introduce a liquid into the connection flow path,
the method provided with:
a first priming step of supplying a first liquid from the introduction flow path to the connection flow path, and performing priming on the microparticle recovery flow path by the first liquid; and
a second priming step of allowing a second liquid to flow from the sheath liquid flow path to the joined flow path, and performing priming on the branching flow path by the second liquid.

The first liquid may be a buffer solution.
The first liquid may include a protein that regulates a colloidal osmotic pressure.
The second priming step may be performed while continuing the supply of the first liquid to the connection flow path at the first priming step.
The joined flow path may include a sort discrimination unit used for performing sort discrimination of a microparticle.
At the first priming step, the joined flow path may be primed by the first liquid.
At the first priming step, a recovery container of a microparticle that flows toward the microparticle recovery flow path may be primed by the first liquid.
At the first priming step, a container into which a sample liquid is introduced may be primed by the first liquid.
At the second priming step, the joined flow path may be primed by the second liquid.
After performing the priming method, a microparticle may be sorted using the microparticle sorting microchip.
After performing the priming method, a sample liquid may be introduced into a first liquid supply container for supplying the first liquid to the sample liquid flow path, and thereafter, a microparticle included in the sample liquid may be sorted using the microparticle sorting microchip.

The sample liquid may be aseptically introduced into the first liquid supply container.

The microparticle may be a biological particle.

The microparticle may be a cell.

Furthermore, the present technology also provides a microparticle sorting method in the microparticle sorting microchip, the method provided with:
a first priming step of supplying a first liquid from the introduction flow path to the connection flow path, and performing priming on the microparticle recovery flow path by the first liquid;
a second priming step of allowing a second liquid to flow from the sheath liquid flow path to the joined flow path, and performing priming on the branching flow path by the second liquid; and
a microparticle sort step of sorting a microparticle using the microparticle sorting microchip after the second priming step.

Furthermore, the present technology also provides a microparticle sorting device that executes,
on the microparticle sorting microchip,
a first priming step of supplying a first liquid from the introduction flow path to the connection flow path, and performing priming on the microparticle recovery flow path by the first liquid; and
a second priming step of allowing a second liquid to flow from the sheath liquid flow path to the joined flow path, and performing priming on the branching flow path by the second liquid.

Furthermore, the present technology also provides a program for allowing a microparticle sorting device to execute, in the microparticle sorting microchip,
a first priming step of supplying a first liquid from the introduction flow path to the connection flow path, and performing priming on the microparticle recovery flow path by the first liquid; and
a second priming step of allowing a second liquid to flow from the sheath liquid flow path to the joined flow path, and performing priming on the branching flow path by the second liquid.

MODE FOR CARRYING OUT THE INVENTION

Hereinafter, a preferred mode for carrying out the present technology is described. Note that, embodiments hereinafter described are representative embodiments of the present technology, and the scope of the present technology is not limited only to them. Note that, the present technology is described in the following order.

1. First embodiment (priming method)
(1) Description of first embodiment
(2) Microparticle sorting microchip and microparticle sorting operation using the same
(2-1) Flow step
(2-2) Determination step
(2-3) Recovery step
(2-4) Microparticle sorting microchip and microparticle
(3) Priming method of the present technology
(3-1) Setting of microparticle sorting microchip to be primed in microparticle sorting device
(3-2) First priming step
(3-3) Second priming step
(3-4) Microparticle sort step
(3-5) First liquid and second liquid
(3-6) Other steps
2. Second embodiment (microparticle sorting method)
3. Third embodiment (microparticle sorting device)
4. Fourth embodiment (program)
5. Example 1. First Embodiment (Priming Method)

(1) Description of First Embodiment

A priming method of the present technology is performed in a microparticle sorting microchip including a specific flow path structure, and includes a first priming step and a second priming step described below. By performing these two steps, the microparticle sorting microchip may be efficiently primed.

Hereinafter, the microparticle sorting microchip and a microparticle sorting operation using the same are first described, and each step performed in the priming method of the present technology is next described.

Figure 1:
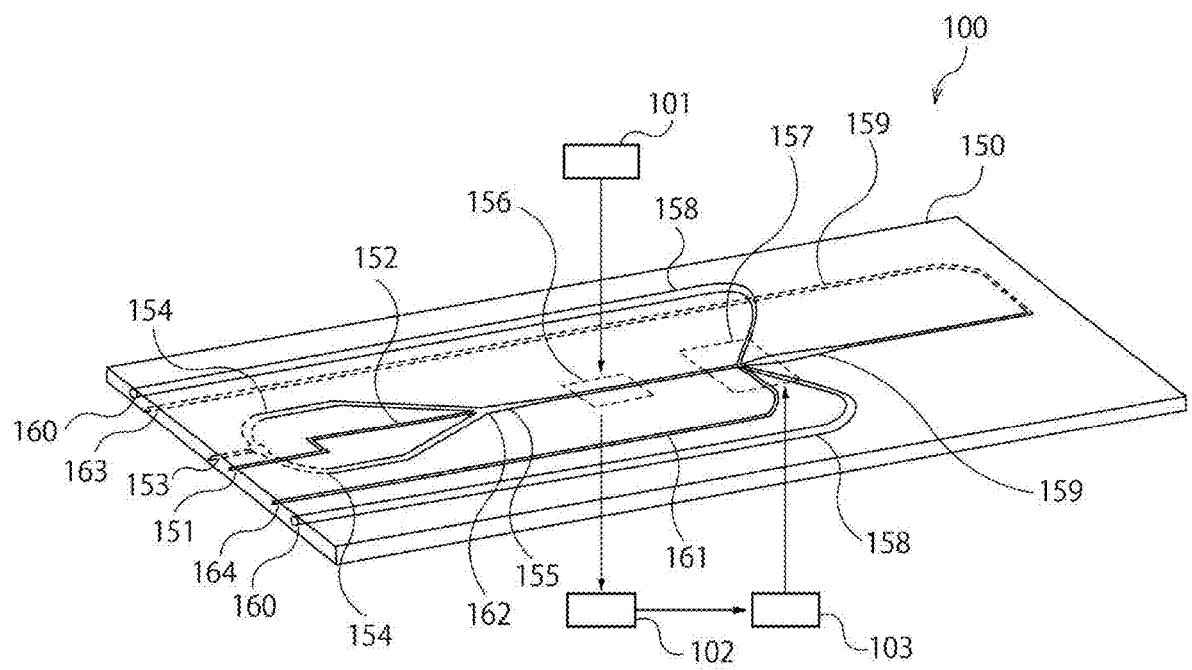
FIG. 1 is a view illustrating a configuration example of a microparticle sorting microchip used in the present technology.
Figure 2:
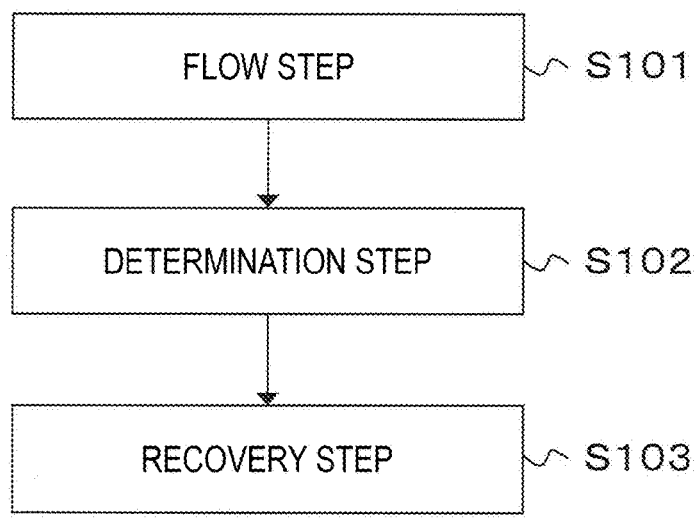
FIG. 2 is a view illustrating an example of a flow of microparticle sorting processing using the microparticle sorting microchip used in the present technology.

(2) Microparticle Sorting Microchip and Microparticle Sorting Operation Using the Same FIG. 1 is a schematic diagram of an example of a flow path structure of the microparticle sorting microchip used in the present technology. FIG. 2 illustrates an example of a flow chart of a sorting operation using the microparticle sorting microchip.

A microparticle sorting microchip 150 illustrated in FIG. 1 includes a sample liquid flow path 152 and a sheath liquid flow path 154 that joins the sample liquid flow path 152 at a junction 162. The microparticle sorting microchip 150 is further provided with a sample liquid inlet 151 and a sheath liquid inlet 153.

Note that, in FIG. 1, a part of the sheath liquid flow path 154 is indicated by a dotted line. The part indicated by the dotted line is located in a position lower than that of the sample liquid flow path 152 indicated by a solid line (position displaced in an optical axis direction to be described later), and the flow paths are not communicated with each other in a position in which the flow path indicated by the dotted line intersect with the flow path indicated by the solid line. Furthermore, in FIG. 1, the sample liquid flow path 152 is illustrated to bend twice between the sample liquid inlet 151 and the junction 162, which facilitates distinction between the sample liquid flow path 152 and the sheath liquid flow path 154. The sample liquid flow path 152 may be formed linearly without bending in this manner between the sample liquid inlet 151 and the junction 162.

In the microparticle sorting operation, a sample liquid including microparticles is introduced from the sample liquid inlet 151 into the sample liquid flow path 152, and a sheath liquid not including the microparticles is introduced from the sheath liquid inlet 153 into the sheath liquid flow path 154.

The microparticle sorting microchip 150 includes a joined flow path 155 including the junction 162 on one end thereof. The joined flow path 155 includes a sort discrimination unit 156 used for performing sort discrimination of the microparticles.

The sample liquid and the sheath liquid join at the junction 162, then flow in the joined flow path 155 toward a particle sort unit 157. Especially, the sample liquid and the sheath liquid join at the junction 162 to form, for example, a laminar flow in which the sample liquid is surrounded by the sheath liquid. Preferably, in the laminar flow, the microparticles are arrayed substantially in a line. Due to the flow path structure in which the sample liquid flow path 152 and two sheath liquid flow paths 154 join at the junction 162, the flow path structure including the joined flow path 155 one end of which is the junction 162, the laminar flow including the microparticles that flow substantially in a line is formed. Therefore, in light irradiation in the sort discrimination unit (also referred to as a detection area) 156 to be described below, it becomes easy to distinguish light generated when irradiating one microparticle with light from light generated when irradiating other microparticles with light.

Figure 3:
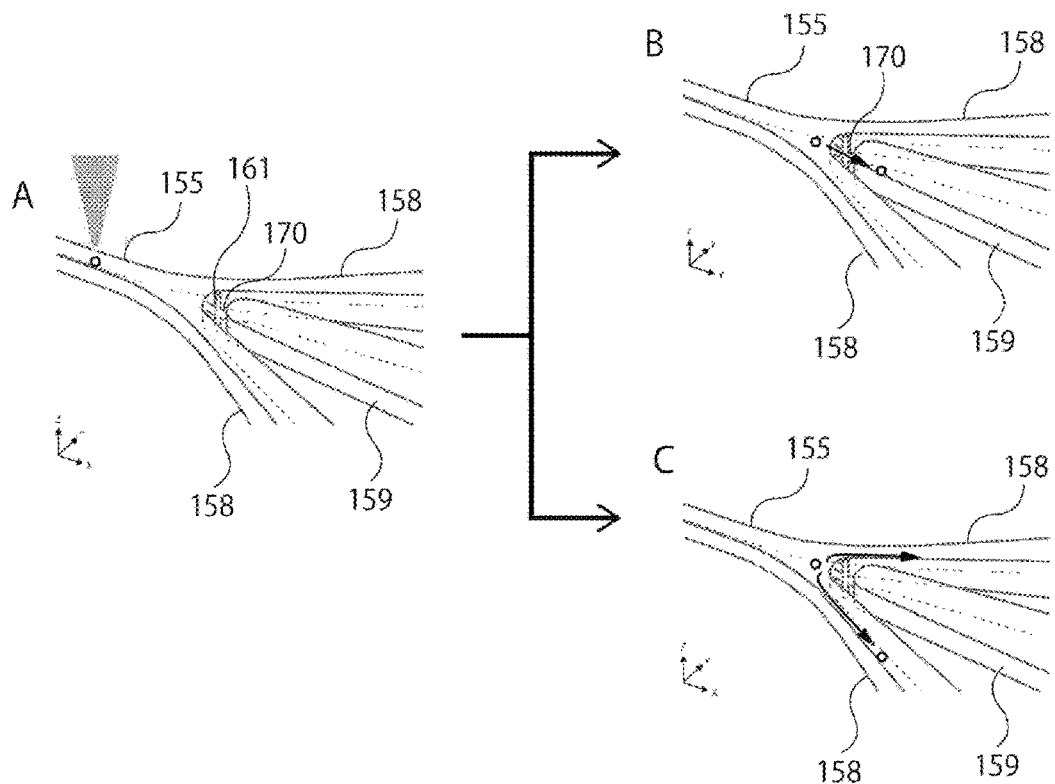
FIG. 3 is an enlarged view of an example of a particle sort unit of the microparticle sorting microchip used in the present technology.

The microparticle sorting microchip 150 further includes the particle sort unit 157 at the other end of the joined flow path 155. FIG. 3 is an enlarged view of the particle sort unit 157. As illustrated in FIG. 3A, at the other end, the joined flow path 155 is connected to a microparticle recovery flow path 159 via a connection flow path 170. As illustrated in FIG. 3A, the joined flow path 155, the connection flow path 170, and the microparticle recovery flow path 159 may be coaxial with each other.

In a case where a recovery target particle flows to the particle sort unit 157, as illustrated in FIG. 3B, a flow from the joined flow path 155 through the connection flow path 170 to enter the microparticle recovery flow path 159 is formed, and the recovery target particle is recovered into the microparticle recovery flow path 159. In this manner, the recovery target particle flows through the connection flow path 170 to the microparticle recovery flow path 159.

In a case where the microparticle that is not the recovery target particle flows to the particle sort unit 157, the microparticle that is not the recovery target particle flows to a branching flow path 158 as illustrated in FIG. 3C. In this case, the flow entering the microparticle recovery flow path 159 is not formed.

As illustrated in FIG. 1, the microparticle recovery flow path 159 is formed so as to extend linearly from the particle sort unit 157, make a U-turn, then reach the same surface as a surface on which the sample liquid inlet 151 and the sheath liquid inlet 153 are formed. The liquid that flows through the microparticle recovery flow path 159 is discharged out of the chip from a recovery flow path terminal 163.

As illustrated in FIG. 1, the two branching flow paths 158 are also formed so as to extend linearly from the particle sort unit 157, make a U-turn, then reach the same surface as the surface on which the sample liquid inlet 151 and the sheath liquid inlet 153 are formed. The liquid that flows through the branching flow path 158 is discharged out of the chip from a branching flow path terminal 166.

In FIG. 1, a display method of the microparticle recovery flow path 159 is changed to a solid line and a dotted line at the U-turn. This change indicates that the position in the optical axis direction changes on the way. By changing the position in the optical axis direction in this manner, the microparticle recovery flow path 159 and the branching flow path 158 are not communicated with each other in a portion intersecting with the branching flow path 158.

Both the recovery flow path terminal 163 and two branching flow path terminals 166 are formed on the surface on which the sample liquid inlet 151 and the sheath liquid inlet 153 are formed. Moreover, an introduction flow path inlet 164 for introducing a liquid into an introduction flow path 161 is also formed on the surface. In this manner, in the microparticle sorting microchip 150, all of the inlets from which the liquid is introduced and outlets from which the liquid is discharged are formed on one surface. This facilitates attachment of the chip to a microparticle sorting device 100. For example, as compared with a case where the inlets and/or outlets are formed on two or more surfaces, connection between flow paths provided on the microparticle sorting device 100 and the flow paths of the microparticle sorting microchip 150 becomes easy.

As illustrated in FIGS. 1 and 3, the microparticle sorting microchip 150 includes the introduction flow path 161 for introducing the liquid into the connection flow path 170.

By introducing the liquid from the introduction flow path 161 into the connection flow path 170, the connection flow path 170 is filled with the liquid. This makes it possible to prevent an unintended microparticle from entering the microparticle recovery flow path 159.

The microparticle sorting microchip 150 includes two branching flow paths 158 connected to the joined flow path 155 at the other end of the joined flow path 155. In this manner, in the microparticle sorting microchip used in the present technology, the joined flow path may be branched into the connection flow path and the at least one branching flow path.

The microparticle other than the recovery target particle flows to either of the two branching flow paths 158 without entering the microparticle recovery flow path 159.

Figure 4:
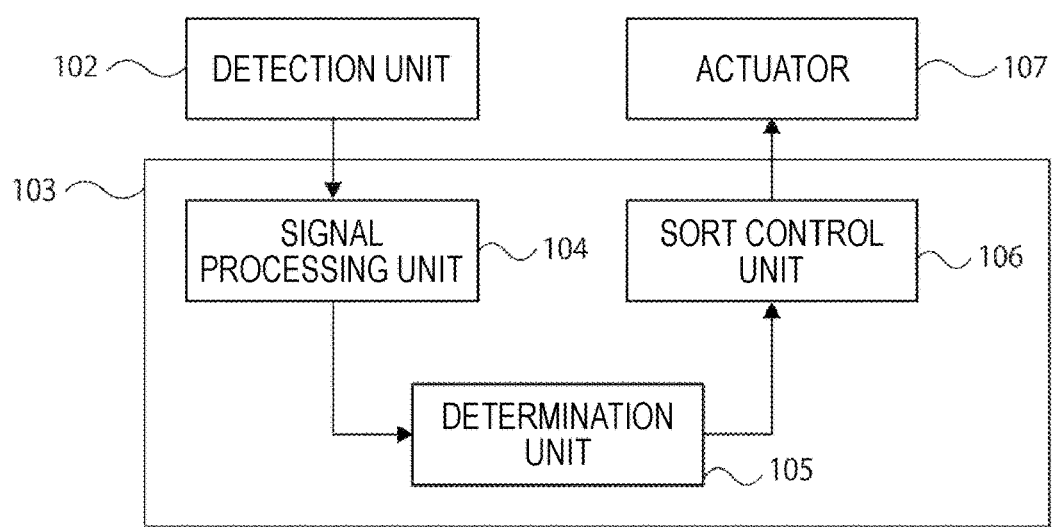
FIG. 4 is a block diagram of an example of a control unit.

Furthermore, as illustrated in FIG. 1, the microparticle sorting microchip 150 forms a part of the microparticle recovery device 100 including a light irradiation unit 101, a detection unit 102, and a control unit 103 in addition to the microchip. As illustrated in FIG. 4, the control unit 103 may include a signal processing unit 104, a determination unit 105, and a sort control unit 106.

As illustrated in FIG. 2, the microparticle sorting operation using the microparticle sorting microchip 150 includes a flow step S101 of allowing the liquid including the microparticles to flow through the joined flow path 155, a determination step S102 of determining whether or not the microparticle that flows through the joined flow path 155 is the recovery target particle, and a recovery step S103 of recovering the recovery target particle into the microparticle recovery flow path 159.

Each step is described below.

(2-1) Flow Step

At the flow step S101, the sample liquid including the microparticles and the sheath liquid not including the microparticles are introduced from the sample liquid inlet 151 and the sheath liquid inlet 153 into the sample liquid flow path 152 and the sheath liquid flow path 154, respectively.

The sample liquid and the sheath liquid join at the junction 162 to form, for example, the laminar flow in which the sample liquid is surrounded by the sheath liquid. Preferably, in the laminar flow, the microparticles are arrayed substantially in a line. That is, at the flow step S101, the laminar flow including the microparticles that flow substantially in a line may be formed.

In this manner, at the flow step S101, the liquid including the microparticles is allowed to flow in the joined flow path 155, especially as the laminar flow. The liquid flows in the joined flow path 155 from the junction 162 toward the particle sort unit 157.

(2-2) Determination Step

At the determination step S102, it is determined whether or not the microparticle that flows through the joined flow path 155 is the recovery target particle. The determination may be made by the determination unit 105. The determination unit 105 may make the determination on the basis of the light generated by the irradiation of the microparticle with light by the light irradiation unit 101. An example of the determination step S102 is described below in further detail.

At the determination step S102, the light irradiation unit 101 irradiates the microparticle that flows through the joined flow path 155 (especially, the sort discrimination unit 156) in the microparticle sorting microchip 150 with light (for example, excitation light), and the detection unit 102 detects the light generated by the light irradiation. On the basis of characteristics of the light detected by the detection unit 102, the determination unit 105 determines whether or not the microparticle is the recovery target particle. For example, the determination unit 105 may make a determination based on scattered light, a determination based on fluorescence, or a determination based on an image (for example, a dark field image or/and a bright field image). At the recovery step S103 described later, the control unit 103 controls the flow in the microparticle sorting microchip 150, so that the recovery target particle is recovered into the microparticle recovery flow path 159.

The light irradiation unit 101 irradiates the microparticle that flows in the flow path in the microparticle sorting microchip 150 with light (for example, excitation light). The light irradiation unit 101 may include a light source that emits light, and an objective lens that condenses the excitation light on the microparticle that flows through the sort discrimination unit. The light source may be appropriately selected by one skilled in the art depending on a purpose of an analysis, and may be, for example, a laser diode, an SHG laser, a solid-state laser, a gas laser, a high brightness LED, or a halogen lamp, or may be a combination of two or more of them. The light irradiation unit may include other optical elements as needed in addition to the light source and the objective lens.

In one embodiment of the present technology, the detection unit 102 detects scattered light and/or fluorescence generated from the microparticle by the light irradiation by the light irradiation unit 101. The detection unit 102 may include a condensing lens that condenses the fluorescence and/or scattered light generated from the microparticle and a detector. As the detector, a PMT, a photodiode, a CCD, a CMOS and the like may be used, but this is not limited thereto. The detection unit 102 may include other optical elements as needed in addition to the condensing lens and the detector. The detection unit 102 may further include, for example, a spectroscopic unit. Examples of optical components that form the spectroscopic unit may include a grating, a prism, and an optical filter, for example. The spectroscopic unit may detect, for example, light having a wavelength that should be detected separately from light having another wavelength. The detection unit 102 may convert the detected light into an analog electric signal by photoelectric conversion. The detection unit 102 may further convert the analog electric signal into a digital electric signal by AD conversion.

In another embodiment of the present technology, the detection unit 102 may obtain an image generated by the light irradiation by the light irradiation unit 101. The image may be, for example, a dark field image, a bright field image, or both of them. In this embodiment, the light irradiation unit 101 may include, for example, a halogen lamp or a laser, and the detection unit 102 may include a CCD or a CMOS. The detection unit 102 may be, for example, an imaging element obtained by stacking a substrate incorporating a CMOS sensor and a substrate incorporating a digital signal processor (DSP). By allowing the DSP of the imaging element to operate as a machine learning unit, the imaging element may operate as a so-called AI sensor. The detection unit 102 including the imaging element may determine whether or not the microparticle is the recovery target particle, for example, on the basis of a learning model. Furthermore, the learning model may be updated in real time while the method according to the present technology is performed. For example, the DSP may perform machine learning processing during reset of a pixel array unit in the CMOS sensor, exposure of the pixel array unit, or readout of a pixel signal from each unit pixel of the pixel array unit. As an example of the imaging element that operates as the AI sensor, there may be, for example, the imaging device disclosed in International Publication No. 2018/051809.

The signal processing unit 104 included in the control unit 103 may process a waveform of the digital electric signal obtained by the detection unit 102 to generate information (data) regarding characteristics of the light used for the determination by the determination unit 105. As the information regarding the characteristics of the light, the signal processing unit 104 may obtain, for example, one, two, or three of a width of the waveform, a height of the waveform, and an area of the waveform from the waveform of the digital electric signal. Furthermore, the information regarding the characteristics of the light may include, for example, a time when the light is detected. The above-described processing by the signal processing unit 104 may be performed especially in the embodiment in which the scattered light and/or fluorescence is detected.

On the basis of the light generated by irradiating the microparticle that flows in the flow path with light, the determination unit 105 included in the control unit 103 determines whether or not the microparticle is the recovery target particle.

In the embodiment in which the scattered light and/or fluorescence is detected, the waveform of the digital electric signal obtained by the detection unit 102 is processed by the control unit 103, then, on the basis of the information regarding the characteristics of the light generated by the processing, the determination unit 105 determines whether or not the microparticle is the recovery target particle. For example, in the determination based on the scattered light, characteristics of an outer shape and/or an internal structure of the microparticle may be specified, and it may be determined whether or not the microparticle is the recovery target particle on the basis of the characteristics. Moreover, for example, by performing pretreatment on the microparticle such as a cell in advance, it is possible to determine whether or not the microparticle is the recovery target particle on the basis of the characteristics similar to those used in flow cytometry. Furthermore, for example, by labeling the microparticle such as the cell with an antibody or a dye (especially, a fluorescent dye), it is possible to determine whether or not the microparticle is the recovery target particle on the basis of the characteristics of a surface antigen of the microparticle.

In the embodiment in which the image is obtained, the determination unit 105 included in the control unit 103 determines whether or not the microparticle is the recovery target particle on the basis of the obtained image (for example, the dark field image, bright field image, or both of them). For example, it may be determined whether or not the microparticle is the recovery target particle on the basis of one or a combination of two or more of the form, size, and color of the microparticle (especially, the cell).

The determination may be made, for example, by whether or not the information regarding the characteristics of the light meets a standard designated in advance. The standard may be a standard indicating that the microparticle is the recovery target particle. The standard may be appropriately set by one skilled in the art, and may be the standard regarding the characteristics of the light such as the standard used in the technical field of the flow cytometry and the like, for example.

One position in the sort discrimination unit 156 may be irradiated with one light, or each of a plurality of positions in the sort discrimination unit 156 may be irradiated with light. For example, the microchip 150 may be formed such that each of two different positions in the sort discrimination unit 156 is irradiated with the light (that is, there are two positions irradiated with the light in the sort discrimination unit 156). In this case, for example, it may be determined, on the basis of the light generated by irradiating the microparticle in one position with light (for example, fluorescence and/or scattered light), whether or not the microparticle is the recovery target particles. Moreover, a speed of the microparticle in the flow path may be calculated on the basis of a difference between the detection time of the light generated by the light irradiation in the one position and the detection time of the light generated by the light irradiation in another position. For this calculation, a distance between the two irradiation positions may be determined in advance, and the speed of the microparticle may be determined on the basis of the difference between the two detection times and the distance. Moreover, on the basis of the speed, an arrival time at the particle sort unit 157 described below may be accurately predicted. By accurately predicting the arrival time, it is possible to optimize a timing of forming the flow entering the microparticle recovery flow path 159. Furthermore, in a case where a difference between the arrival time of a certain microparticle at the particle sort unit 157 and the arrival time of the microparticle before or after the certain microparticle at the particle sort unit 157 is equal to or smaller than a predetermined threshold, it is also possible to determine that the certain microparticle is not recovered. In a case where the distance between the certain microparticle and the microparticle before or after the same is short, a possibility that, when the certain microparticle is sucked, the microparticle before or after the same is recovered together increases. By determining that the certain microparticle is not recovered in a case where the possibility that the microparticle is recovered together is high, it is possible to prevent the microparticle before or after the same from being recovered. This makes it possible to increase purity of the target microparticles among the recovered microparticles. Specific examples of the microchip in which each of two different positions in the sort discrimination unit 156 is irradiated with light and the device including the microchip are disclosed in, for example, Japanese Patent Application Laid-Open No. 2014-202573.

Note that, the control unit 103 may control the light irradiation by the light irradiation unit 101 and/or the light detection by the detection unit 102. Furthermore, the control unit 103 may control drive of a pump for supplying a fluid into the microparticle sorting microchip 150. The control unit 103 may include, for example, a hard disk in which a program for allowing the microparticle sorting device 100 to execute the priming method according to the present technology and an OS are stored, a CPU, and a memory. For example, a function of the control unit 103 may be implemented in a general-purpose computer. The program may be recorded on a recording medium such as a microSD memory card, an SD memory card, or a flash memory, for example. The program recorded on the recording medium may be read out by a drive (not illustrated) provided in the microparticle sorting device 100, then the control unit 103 may allow the microparticle sorting device 100 to execute the priming method according to the present technology and the microparticle sorting operation performed thereafter according to the read out program.

(2-3) Recovery Step

At the recovery step S103, the microparticle determined to be the recovery target particle at the determination step S102 is recovered into the microparticle recovery flow path 159. The recovery step S103 is performed in the particle sort unit 157 in the microchip 150. In the particle sort unit 157, the laminar flow that flows through the joined flow path 155 flows to the two branching flow paths 158 separately. The particle sort unit 157 illustrated in FIG. 1 includes the two branching flow paths 158, but the number of the branching flow paths is not limited to two. The particle sort unit 157 may be provided with, for example, one or a plurality of (for example, two, three, or four) branching flow paths. The branching flow path may be formed to branch into a Y shape on one plane as illustrated in FIG. 1, or may be formed to branch three-dimensionally.

Figure 5A:
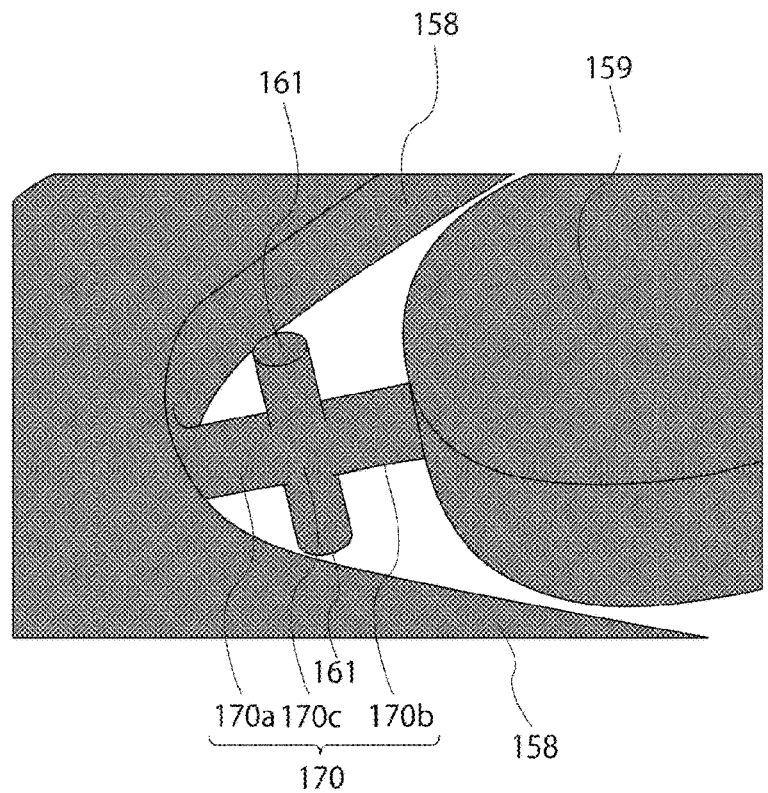
FIG. 5A is an enlarged view of a connection flow path portion.
Figure 5B:
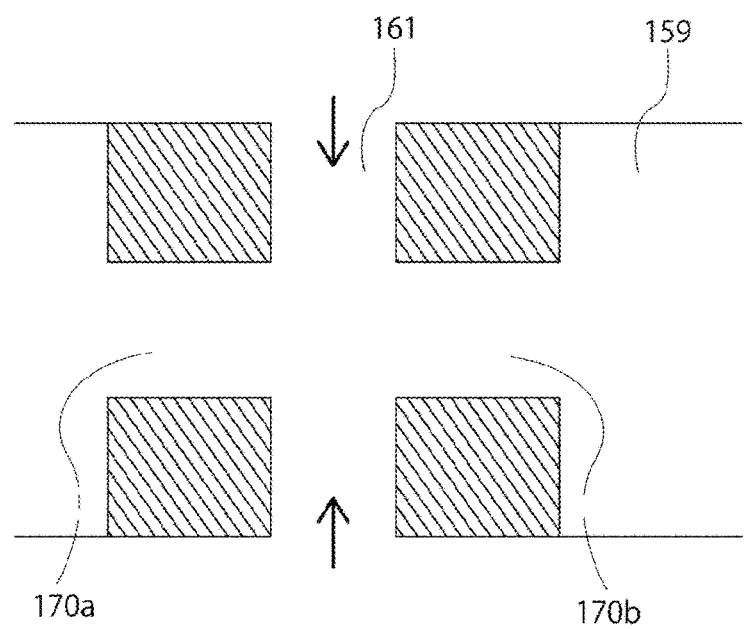
FIG. 5B is an enlarged view of a connection flow path portion.

FIGS. 5A and 5B are enlarged views of the vicinity of the connection flow path 170. FIG. 5A is a schematic perspective view of the vicinity of the connection flow path 170.

FIG. 5B is a schematic cross-sectional view on a plane passing through a center line of the introduction flow path 161 and a center line of the connection flow path 170. The connection flow path 170 includes a flow path 170a on a side of the sort discrimination unit 156 (hereinafter, also referred to as an upstream side connection flow path 170a), a flow path 170b on a side of the microparticle recovery flow path 159 (hereinafter, also referred to as a downstream side connection flow path 170b), and a connection 170c between the connection flow path 170 and the introduction flow path 161. The introduction flow path 161 is provided so as to be substantially perpendicular to an axis of the flow path of the connection flow path 170. In FIGS. 5A and 5B, two introduction flow paths 161 are provided so as to face each other in substantially the center position of the connection flow path 170, but it is also possible that only one introduction flow path is provided.

A shape and a dimension of a cross-section of the upstream side connection flow path 170a may be the same as a shape and a dimension of the downstream side connection flow path 170b. For example, as illustrated in FIGS. 5A and 5B, both the cross-section of the upstream side connection flow path 170a and the cross-section of the downstream side connection flow path 170b may be substantially circular with the same dimension. Alternatively, both the two cross-sections may be rectangles (for example, squares or rectangles) having the same dimension.

The liquid is supplied from the two introduction flow paths 161 to the connection flow path 170 as indicated by arrows in FIG. 5B. The liquid flows from the connection 170c to both the upstream side connection flow path 170a and the downstream side connection flow path 170b.

In a case where the recovery step is not performed, the liquid flows as follows.

The liquid that flows to the upstream side connection flow path 170a exits from a connection surface to the joined flow path 155 of the connection flow path 170, and then flows separately to the two branching flow paths 158. Since the liquid exits the connection surface in this manner, it is possible to prevent the liquid and the microparticle that do not need to be recovered into the microparticle recovery flow path 159 from entering the microparticle recovery flow path 159 through the connection flow path 170.

The liquid that flows to the downstream side connection flow path 170b flows into the microparticle recovery flow path 159. Therefore, the microparticle recovery flow path 159 is filled with the liquid.

Also in a case where the recovery step is performed, the liquid may be supplied from the two introduction flow paths 161 to the connection flow path 170. However, due to pressure fluctuation in the microparticle recovery flow path 159, especially, by generating a negative pressure in the microparticle recovery flow path 159, a flow from the joined flow path 155 through the connection flow path 170 to the microparticle recovery flow path 159 is formed. That is, a flow is formed from the joined flow path 155 through the upstream side connection flow path 170a, the connection 170c, and the downstream side connection flow path 170b in this order to the microparticle recovery flow path 159. Therefore, the recovery target particle is recovered into the microparticle recovery flow path 159.

Figure 6A:
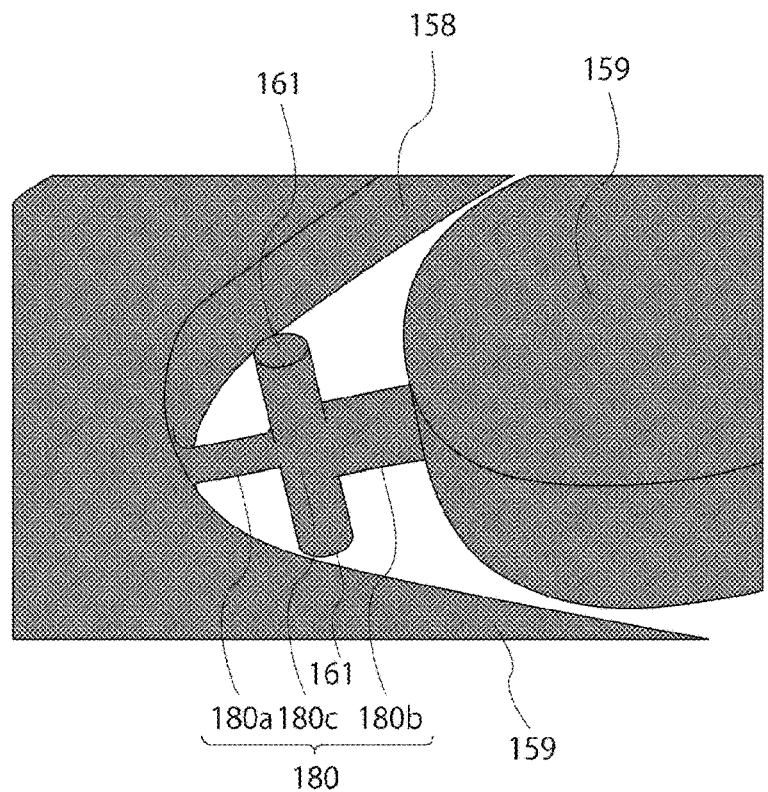
FIG. 6A is an enlarged view of a connection flow path portion.
Figure 6B:
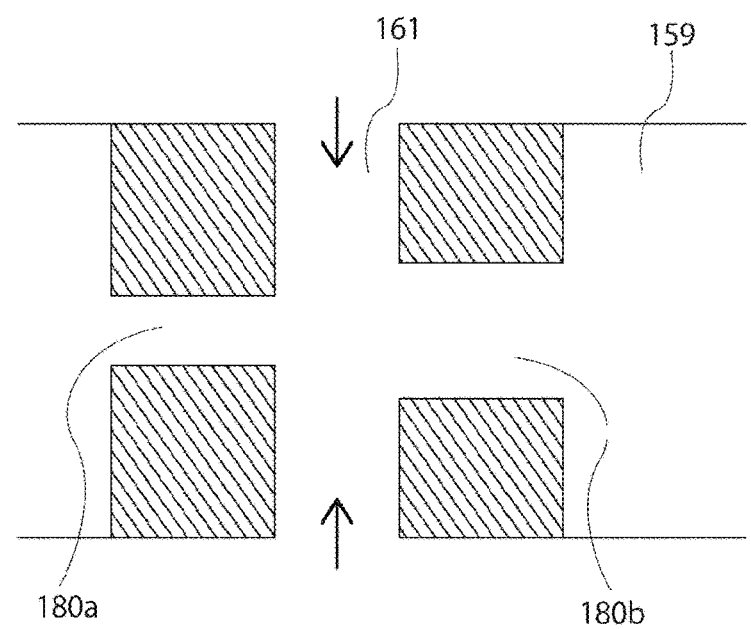
FIG. 6B is an enlarged view of a connection flow path portion.

The shape and/or dimension of the cross-section of the upstream side connection flow path 170a may be different from the shape and/or dimension of the downstream side connection flow path 170b. Examples in which the dimensions of the two flow paths are different from each other are illustrated in FIGS. 6A and 6B. As illustrated in FIGS. 6A and 6B, a connection flow path 180 includes a flow path 180a on a side of the sort discrimination unit 156 (hereinafter, also referred to as an upstream side connection flow path 180a), a flow path 180b on a side of the microparticle recovery flow path 159 (hereinafter, also referred to as a downstream side connection flow path 180b), and a connection 180c between the connection flow path 180 and the introduction flow path 161. Both a cross-section of the upstream side connection flow path 180a and a cross-section of the downstream side connection flow path 180b have substantially circular shapes, but a diameter of the cross-section of the latter is larger than a diameter of the cross-section of the former. By making the diameter of the cross-section of the latter larger than that of the former, as compared with a case where the diameters of both are the same, it is possible to more effectively prevent the recovery target particle already sorted into the microparticle recovery flow path 159 from being emitted to the joined flow path 155 through the connection flow path 180 immediately after the microparticle sorting operation by the negative pressure described above.

For example, in a case where both the cross-section of the upstream side connection flow path 180a and the cross-section of the downstream side connection flow path 180b are rectangular, by making an area of the cross-section of the latter larger than an area of the cross-section of the former, it is possible to more effectively prevent the already recovered microparticle from being emitted to the joined flow path 155 through the connection flow path 180 as described above.

At the recovery step S103, due to the pressure fluctuation in the microparticle recovery flow path 159, the recovery target particle is recovered into the microparticle recovery flow path through the connection flow path. The recovery may be performed, for example, by generating the negative pressure in the microparticle recovery flow path 159 as described above. The negative pressure may be generated, for example, when a wall defining the microparticle recovery flow path 159 is deformed by an actuator 107 (especially, a piezo actuator) attached to an outer side of the microchip 150. The negative pressure may form the flow entering the microparticle recovery flow path 159. In order to generate the negative pressure, the actuator 107 may be attached to the outer side of the microchip 150, for example, so that the wall of the microparticle recovery flow path 159 may be deformed. Due to the deformation of the wall, an inner space of the microparticle recovery flow path 159 is changed, and the negative pressure may be generated. The actuator 107 may be, for example, the piezo actuator. When the recovery target particle is sucked into the microparticle recovery flow path 159, the sample liquid that forms the laminar flow or the sample liquid and the sheath liquid that form the laminar flow may also flow to the microparticle recovery flow path 159. In this manner, the recovery target particle is sorted in the particle sort unit 157 and recovered into the microparticle recovery flow path 159.

The connection flow path 170 is provided with the introduction flow path 161 in order to prevent the microparticle that is not the recovery target particle from entering the microparticle recovery flow path 159 through the connection flow path 170. The liquid is introduced into the connection flow path 170 from the introduction flow path 161. By the introduction of the liquid, the connection flow path 170 is filled with the liquid. Moreover, since a flow from the connection flow path 170 to the joined flow path 155 is formed by a part of the liquid, it is possible to prevent the microparticle other than the recovery target particle from entering the microparticle recovery flow path 159. The liquid that forms the flow from the connection flow path 170 to the joined flow path 155 flows, by the flow of the liquid that flows through the joined flow path 155 to the branching flow path 158, through the branching flow path 158 in a manner similar to the liquid without flowing in the joined flow path 155.

Note that, the rest of the liquid introduced into the connection flow path 170 flows to the microparticle recovery flow path 159. Therefore, the microparticle recovery flow path 159 may be filled with the liquid.

The flow that flows to the branching flow path 158 may be discharged out of the microchip at the branching flow path terminal 160. Furthermore, the recovery target particle recovered into the microparticle recovery flow path 159 may be discharged out of the microchip at the recovery flow path terminal 161. A container may be connected to the recovery flow path terminal 161 via a flow path such as a tube. The recovery target particle may be recovered into the container.

As illustrated in FIGS. 1 and 3, in the microparticle sorting microchip used in the present technology, the joined flow path, the connection flow path, and the recovery flow path may be linearly arranged. In a case where these three flow paths are arranged linearly (especially, coaxially), it is possible to more effectively perform the recovery step as compared with a case where the connection flow path and the recovery flow path are arranged at an angle with respect to the joined flow path, for example. For example, a suction amount required for guiding the recovery target particle to the connection flow path may be reduced.

Furthermore, in the microparticle sorting microchip used in the present technology, the microparticles are arrayed substantially in a line in the joined flow path and flow toward the connection flow path. Therefore, the suction amount at the recovery step may be reduced.

As described above, in the microparticle sorting microchip used in the present technology, the liquid is supplied from the introduction flow path to the connection flow path. Therefore, a flow from a connection position between the introduction flow path and the connection flow path toward the joined flow path is formed in the connection flow path, and it is possible to prevent the liquid that flows through the joined flow path from entering the connection flow path and prevent the microparticle other than the recovery target particle from flowing to the recovery flow path through the connection flow path. When performing the recovery step, as described above, for example, due to the negative pressure generated in the recovery flow path, the recovery target particle is recovered into the recovery flow path through the connection flow path.

(2-4) Microparticle Sorting Microchip and Microparticle

In the present technology, "micro" means that at least a part of the flow paths included in the microparticle sorting microchip has a dimension of μm order, especially, a cross-sectional dimension of μm order. That is, in the present technology, the "microchip" refers to a chip including the flow path of μm order, especially, a chip including the flow path having the cross-sectional dimension of μm order. For example, a chip including a particle sort unit including the flow path having the cross-sectional dimension of μm order may be referred to as the microchip according to the present technology. For example, in the particle sort unit 157, a cross-section of the joined flow path 155 is, for example, a rectangle, and a width of the joined flow path 155 is, for example, 100 μm to 500 μm, and especially 100 μm to 300 μm in the particle sort unit 157. A width of the branching flow path that branches from the joined flow path 155 may be smaller than the width of the joined flow path 155. The cross-section of the connection flow path 170 is, for example, circular, and the diameter of the connection flow path 170 at the connection between the connection flow path 170 and the joined flow path 155 may be, for example, 10 μm to 60 μm, and especially 20 μm to 50 μm. These dimensions regarding the flow path may be appropriately changed depending on a size of the microparticle, especially, the size of the recovery target particle.

The microparticle sorting microchip 150 may be manufactured by a method known in the art. For example, the biological particle sorting microchip 150 may be manufactured by adhering two or more substrates on which a predetermined flow path is formed. The flow path may be formed on, for example, all of two or more substrates (especially, two substrates), or formed on only a part of the two or more substrates (especially, one of two substrates). In order to more easily adjust a position when the substrates are adhered, it is preferable that the flow path is formed on only one substrate. For example, it is possible to create the flow path structure in which the two flow paths are provided in different positions in the optical axis direction (so as not to be communicated with each other) and so as to intersect with each other in a case of being seen in the optical axis direction as indicated by the dotted line and the solid line in FIG. 1 by stacking three or more substrates on which the flow path is provided.

Materials known in the art may be used as a material for forming the microparticle sorting microchip 150. Examples thereof include, but are not limited to, for example, polycarbonate, cycloolefin polymer, polypropylene, polydimethylsiloxane (PDMS), polymethylmethacrylate (PMMA), polyethylene, polystyrene, glass, and silicon. Especially, polymer materials such as polycarbonate, cycloolefin polymer, and polypropylene, for example, are especially preferable because they are excellent in processability and may manufacture a microchip inexpensively using a molding device.

The microparticle sorting microchip 150 is preferably transparent. For example, in the microparticle sorting microchip 150, at least a portion through which light (laser light and scattered light) passes is transparent, and for example, the sorting discrimination unit may be transparent. An entire microparticle sorting microchip 150 may be transparent.

Note that, in the description above, the embodiment in which the above-described flow path group is formed on the disposable microparticle sorting microchip 150 is described, but in the present technology, it is also possible that the above-described flow path group is not formed on the microchip 150. For example, the above-described flow path group may be formed in a substrate such as plastic or glass, for example. Furthermore, the above-described flow path group may have a two-dimensional or three-dimensional structure.

In the present technology, the microparticle may be the particle having a dimension capable of flowing in the flow path in the microparticle sorting microchip. In the present technology, the microparticle may be appropriately selected by one skilled in the art. In the present technology, the microparticles may include biological microparticles such as cells, cell aggregations, microorganisms, and liposomes; synthetic microparticles such as gel particles, beads, latex particles, polymer particles, and industrial particles and the like.

The biological microparticles (also referred to as biological particles) may include chromosomes, liposomes, mitochondria, organelles (cell organelles) and the like that form various cells. The cells may include animal cells (such as hemocyte cells) and plant cells. The cells may be, especially, blood cells or tissue cells. The blood cells may be floating cells such as T cells and B cells, for example. The tissue cells may be, for example, adherent cultured cells or adherent cells separated from the tissue. The cell aggregations may include, for example, spheroids and organoids. The microorganisms may include bacteria such as *Escherichia coli*, viruses such as tobacco mosaic virus, fungi such as yeast and the like. Moreover, the biological microparticles may also include biological polymers such as nucleic acids, proteins, and complexes thereof. These biological polymers may be, for example, extracted from the cells or may be included in blood samples or other liquid samples.

The synthetic microparticles may be microparticles including, for example, organic or inorganic polymer materials, metal and the like. The organic polymer materials may include polystyrene, styrene-divinylbenzene, polymethyl methacrylate and the like. The inorganic polymer materials may include glass, silica, a magnetic material and the like. The metal may include gold colloid, aluminum and the like. The synthetic microparticles may be, for example, gel particles or beads, and more especially, gel particles or beads to which one or a combination of two or more selected from oligonucleotides, peptides, proteins, and enzymes are bound.

A shape of the microparticle may be spherical or substantial spherical or non-spherical. A size and mass of the microparticle may be appropriately selected by one skilled in the art depending on a size of the flow path of the microchip. In contrast, the size of the flow path of the microchip may be appropriately selected depending on the size and mass of the microparticle. In the present technology, chemical or biological labels such as fluorescent dyes or fluorescent proteins, for example, may be attached to the microparticles as needed. The label may make detection of the microparticle easier. The label that should be attached may be appropriately selected by one skilled in the art. Molecules that specifically react with the microparticles (for example, antibodies, aptamers, DNA, RNA or the like) may bind to the label.

According to one embodiment of the present technology, the microparticle may be the biological particle, especially, the cell.

(3) Priming Method of the Present Technology

Figure 7:
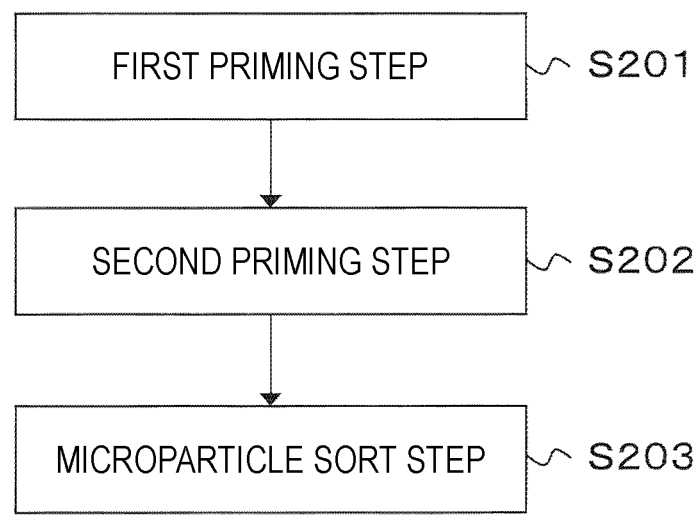
FIG. 7 is an example of a flow chart of a priming method of the present technology.

FIG. 7 illustrates an example of a flow chart of the priming method of the present technology. As illustrated in FIG. 7, the priming method of the present technology includes a first priming step S201 and a second priming step S202. At the first priming step S201, a first liquid is supplied from the introduction flow path to the connection flow path, so that the microparticle recovery flow path is primed by the first liquid. At the second priming step S202, a second liquid is allowed to flow from the sheath liquid flow path to the joined flow path, so that the branching flow path is primed by the second liquid. After these priming steps, a microparticle sort step S203 may be performed. At the microparticle sort step S203, the microparticle sorting operation as described in (2) described above may be performed.

By the priming method of the present technology, all the flow paths of the microparticle sorting microchip described in (2) described above may be efficiently primed. Moreover, the priming method of the present technology may prevent non-specific adsorption of the microparticle to an inner wall of the flow path of the microparticle sorting microchip in the microparticle sorting operation performed after the method is executed. Furthermore, the container into which the microparticle sorted by the microparticle sorting microchip is recovered may also be efficiently primed.

Advantages of the Priming Method of the Present Technology are Further Described Below.

In the microparticle sorting operation using the microparticle sorting microchip, droplet charging is not performed, and the recovery target particle is sorted by suction by, for example, the piezo actuator and the like. Therefore, in the sorting operation, it is not necessary to use a buffer solution for the droplet charging as the sheath liquid, and for example, a buffer solution having a high affinity for the cell and the like may be used as the sheath liquid.

In the microparticle sorting operation using the microparticle sorting microchip, for example, the liquid is introduced from the introduction flow path into the connection flow path, so that the microparticle other than the recovery target particle is prevented from entering the connection flow path, and the recovery target particle is recovered into the microparticle recovery flow path by suction. As the liquid introduced from the introduction flow path into the connection flow path, a liquid including a component preferable for the recovery target particle (for example, the cell and the like) or a component for analyzing the recovery target particle (for example, a serum, an antibody, a protein such as cytokine, and a surfactant) may be used. Therefore, the recovery target particle may be recovered into the liquid according to the purpose.

Regarding the sorting with a droplet charging type flow cytometer, it may be required to prepare, for example, several liters of sheath liquid. Therefore, it is not practical to add an expensive or valuable reagent to the sheath liquid used in the droplet charging type flow cytometer. In contrast, in the microparticle sorting operation using the microparticle sorting microchip, the liquid introduced from the introduction flow path into the connection flow path is used apart from the sheath liquid. A used amount of the liquid may be about several hundred mL. Therefore, it is acceptable to include the expensive or valuable reagent in the liquid.

Furthermore, as a problem regarding the cell sorters in general including the flow cytometer, when the sorted cell arrives at the recovery container, the cell might be damaged by contact or adsorption to an inner surface of the recovery container. In order to prevent the damage, the inner surface of the recovery container may be washed in advance with a liquid including a protein and a surfactant. This is because the inner surface is primed by the liquid, so that the damage is less likely to occur.

Regarding open type cell sorters, the recovery container (for example, a collection tube and the like) may be relatively easily primed prior to the sorting operation. In contrast, the microparticle sorting chip may be used for closed type sorting. In this case, the priming operation of the recovery container cannot be easily performed as in the case of the open type cell sorter. In the priming method of the present technology, the recovery container used in the closed type sorting using the microparticle sorting chip may be easily primed.

Moreover, in the priming method, the amount of the liquid used for the priming of the recovery container may be relatively small. Therefore, it is likely to be acceptable to include the expensive reagent in the liquid.

Hereinafter, the priming method according to the present technology is further described with reference to FIGS. 8 to 11.

Figure 8:
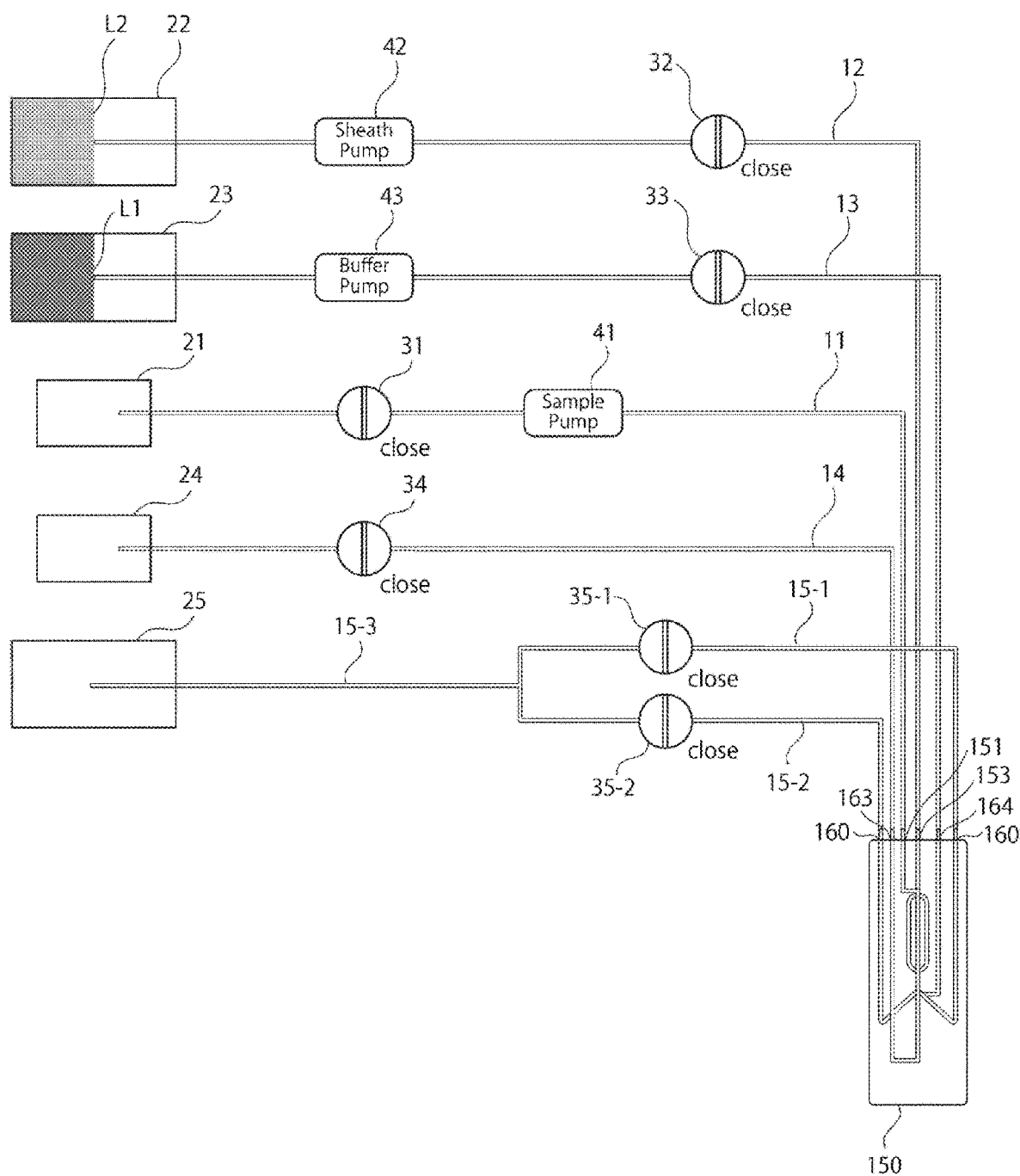
FIG. 8 is a schematic diagram of an example of a state in which a plurality of tubes is connected to the microparticle sorting microchip before a priming method of the present technology is performed.

(3-1) Setting of Microparticle Sorting Microchip to be Primed in Microparticle Sorting Device FIG. 8 is a schematic diagram of a state in which a plurality of tubes is connected to the microparticle sorting microchip before the priming method of the present technology is performed.

First, the microparticle sorting microchip 150 on which the priming method of the present technology is to be performed is set in the microparticle sorting device 100. Before the execution of the priming method starts, all the flow paths of the microparticle sorting microchip 150 may be in a dry state (a state in which the liquid is not brought into contact).

A tube 11 is connected to the sample liquid inlet 151 of the microparticle sorting microchip 150. A valve 31 is provided on the tube 11. The valve 31 may be closed when the microparticle sorting microchip 150 is set in the microparticle sorting device 100 (indicated as "close" in FIG. 7; as for other valves, closed valves are also indicated as "close"). An empty container 21 is connected to the tube 11. Furthermore, a pump 41 is provided on the tube 11. The pump 41 may open the tube 11, and in addition, deliver a liquid from the container 21 to the sample liquid inlet 151 and other way round.

A tube 12 is connected to the sheath liquid inlet 153 of the microparticle sorting microchip 150. A valve 32 is provided on the tube 12. The valve 32 may be closed when the microparticle sorting microchip 150 is set in the microparticle sorting device 100. A container 22 in which a second liquid L2 (sheath liquid) is accommodated is connected to the tube 12. Furthermore, a pump 42 is provided on the tube 12. By driving the pump 42, the sheath liquid in the container 22 may be introduced into the sheath liquid flow path 154 through the sheath liquid inlet 153.

A tube 13 is connected to the introduction flow path inlet 164 that introduces the liquid into the introduction flow path 161 of the microparticle sorting microchip 150. A valve 33 is provided on the tube 13. The valve 33 may be closed when the microparticle sorting microchip 150 is set in the microparticle sorting device 100. A container 23 in which a first liquid L1 (for example, buffer liquid) is accommodated is connected to the tube 13. A pump 43 is provided on the tube 13. By driving the pump 43, the first liquid in the container 23 may be introduced into the introduction flow path 161 through the introduction flow path inlet 164.

A tube 14 is connected to the recovery flow path terminal 163 of the microparticle recovery flow path 159 of the microparticle sorting microchip 150. A valve 34 is provided on the tube 14. The valve 34 may be closed when the microparticle sorting microchip 150 is set in the microparticle sorting device 100. An empty container 24 into which the recovery target particle is recovered is connected to the tube 14.

Tubes 15-1 and 15-2 are connected to the branching flow path terminals 160 of the two branching flow paths 158 of the microparticle sorting microchip 150, and valves 35-1 and 35-2 are provided on the tubes 15-1 and 15-2, respectively. The two tubes 15-1 and 15-2 join to form one tube 15-3, and the tube 15-3 is connected to a waste liquid recovery container 25.

(3-2) First Priming Step

Figure 9:
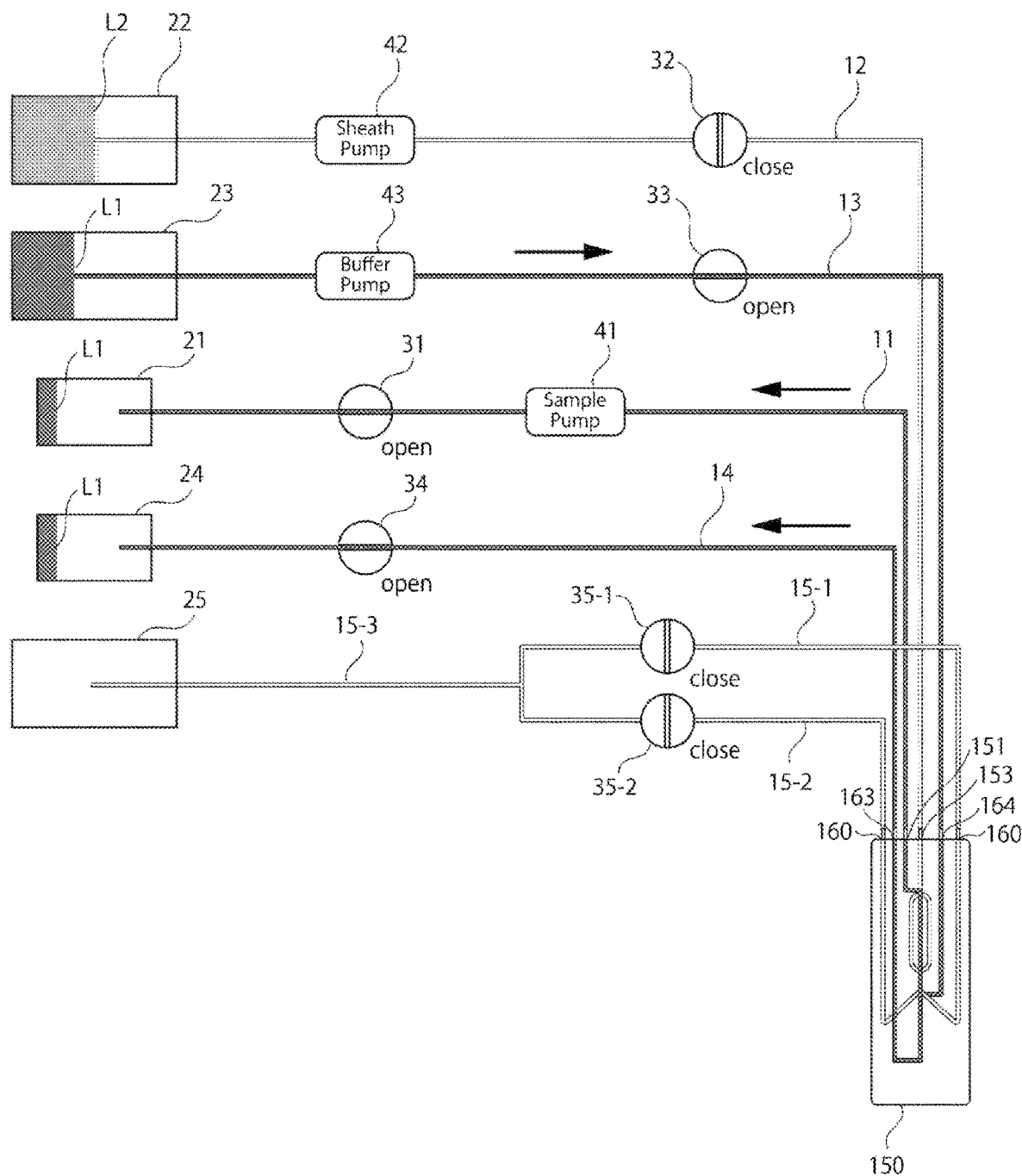
FIG. 9 is a schematic diagram for illustrating a state in which a first priming step of the priming method of the present technology is performed.

FIG. 9 illustrates a state in which the first priming step of the priming method of the present technology is performed.

At the first priming step, the first liquid L1 in the container 23 is supplied from the introduction flow path inlet 164 to the introduction flow path 161 and the connection flow path 170, so that the microparticle recovery flow path 159 is primed by the first liquid L1. The first priming step is hereinafter described in further detail. Note that, the first liquid is described in (3-5) below.

The valves 31, 33, and 34 are opened for performing the first priming step, and the pump 41 opens the tube (indicated as "open" in FIG. 9; the same applies to other valves). The valves 32, 35-1 and 35-2 are closed.

At the first priming step, the pump 43 is driven and the first liquid L1 in the container 23 is delivered to the introduction flow path 161. The first liquid L1 passes through the introduction flow path 161 to arrive at the connection flow path 170. Since both the valves 31 and 34 are opened, the first liquid L1 flows through the connection flow path 170 toward the joined flow path 155 and toward the microparticle recovery flow path 159.

The first liquid L1 that flows toward the joined flow path 155 further flows through the joined flow path 155 toward the sample liquid flow path 152, then passes through the sample liquid flow path 152, the sample liquid inlet 151, and the tube 11, and recovered into the container 21.

The first liquid L1 that flows toward the microparticle recovery flow path 159 is recovered into the container 24 through the microparticle recovery flow path 159 and the tube 14.

In this manner, at the first priming step, the joined flow path 155, the sample liquid flow path 152, and the microparticle recovery flow path 159 are primed by the first liquid L1. This may prevent non-specific adsorption of the microparticle to the joined flow path 155, the sample liquid flow path 152, and the microparticle recovery flow path 159 in the microparticle sorting operation performed after the priming method of the present technology.

At the first priming step, the valves 32, 35-1 and 35-2 are closed. Therefore, the first liquid L1 does not flow through the sheath liquid flow path 154 and the branching flow paths 158-1 and 158-2. That is, at the first priming step, the sheath liquid flow path 154 and the branching flow paths 158-1 and 158-2 are not primed by the first liquid L1.

Furthermore, at the first priming step, the first liquid L1 is recovered into the container 21 through the tube 11. The container 21 is a container into which the sample liquid including the microparticle to be subjected to microparticle sorting processing is introduced. That is, at the first priming step, the container into which the sample liquid is introduced is primed by the first liquid L1. This makes it possible to prevent non-specific adsorption of the microparticle (for example, the cell and the like) in the sample liquid to the sample liquid container.

Furthermore, at the first priming step, the first liquid L1 is recovered into the container 24 through the tube 14. The container 24 is a container into which the recovery target particle is recovered. That is, at the first priming step, the recovery container of the recovery target particle (microparticle that flows to the microparticle recovery flow path 159) is primed by the first liquid L1. This makes it possible to prevent non-specific adsorption of the recovery target particle (for example, the cell and the like) to the recovery container in the microparticle sorting operation performed after the priming method of the present technology.

(3-3) Second Priming Step

Figure 10:
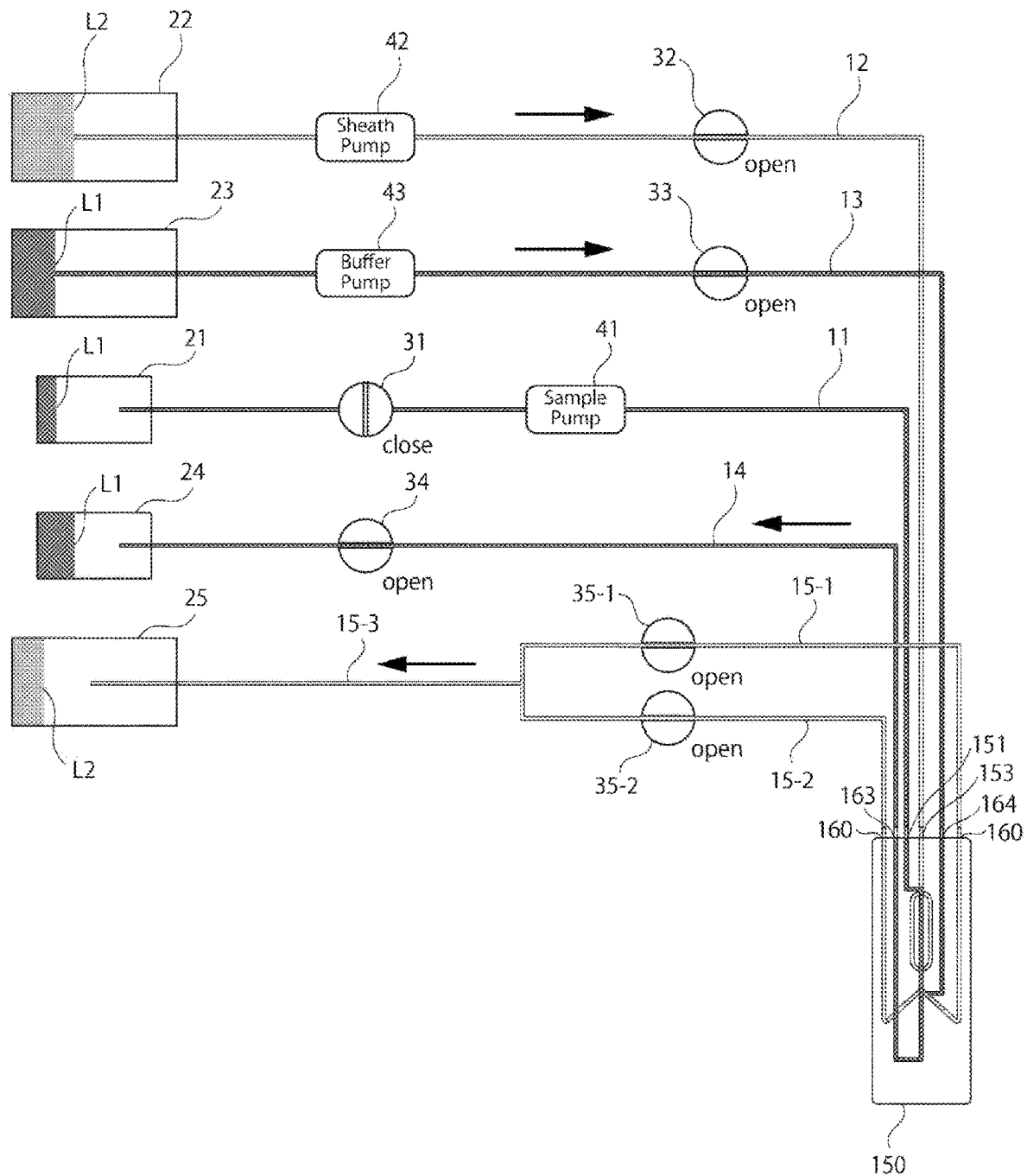
FIG. 10 is a schematic diagram for illustrating a state in which a second priming step of the priming method of the present technology is performed.

FIG. 10 illustrates a state in which the second priming step of the priming method of the present technology is performed.

At the second priming step, the second liquid L2 in the container 22 is allowed to flow from the sheath liquid inlet 153 to the sheath liquid flow path 154 and the joined flow path 155, so that the branching flow paths 158-1 and 158-2 are primed by the second liquid L2. The second priming step is hereinafter described in further detail. Note that, the second liquid L2 is described in (3-5) below.

The valves 32, 33, 34, 35-1, and 35-2 are opened and the valve 31 is closed to perform the second priming step. Furthermore, the pump 41 closes the tube 11.

At the second priming step, the pump 42 is driven and the second liquid L2 in the container 22 is introduced into the sheath liquid flow path 154, then this further flows from the sheath liquid flow path 154 to the joined flow path 155. The second liquid L2 flows through the joined flow path 155 toward the connection flow path 170. Therefore, the joined flow path 155 is primed by the second liquid L2.

Here, the supply of the first liquid L1 to the connection flow path 170 performed at the first priming step may be continued at the second priming step as well. Therefore, the connection flow path 170 and the microparticle recovery flow path 159 are filled with the first liquid L1, moreover, the first liquid L1 flows through the connection flow path 170 toward the joined flow path 155. Therefore, the second liquid L2 that flows through the joined flow path 155 toward the connection flow path 170 separately flows to the branching flow paths 158-1 and 158-2 without entering the connection flow path 170.

Furthermore, since the valve 32 is closed, the sample liquid flow path 152 is filled with the first liquid L1. Therefore, it is also possible to prevent the second liquid L2 from entering the sample liquid flow path 152. Therefore, it is possible that the supply of the first liquid L1 to the connection flow path 170 performed at the first priming step is not performed at the second priming step.

In this manner, at the second priming step, the branching flow path 158 and the sheath liquid flow path 154 are primed by the second liquid L2.

At the second priming step, as described above, the first liquid L1 is continuously supplied to the connection flow path 170. Therefore, the second liquid L2 does not enter the connection flow path 170 and the microparticle recovery flow path 159. That is, at the second priming step, the connection flow path 170 and the microparticle recovery flow path 159 are not primed by the second liquid L2. Therefore, the second liquid L2 is not mixed into the liquid including the recovery target particle recovered into the microparticle recovery flow path 159 by the microparticle sorting operation performed after the priming method of the present technology.

Note that, at the second priming step, the supply of the first liquid L1 to the connection flow path 170 may be stopped, and the valve 34 may be closed instead. By closing the valve 34, it is possible to prevent the second liquid L2 from entering the connection flow path 170 and the microparticle recovery flow path 159.

(3-4) Microparticle Sort Step

Figure 11:
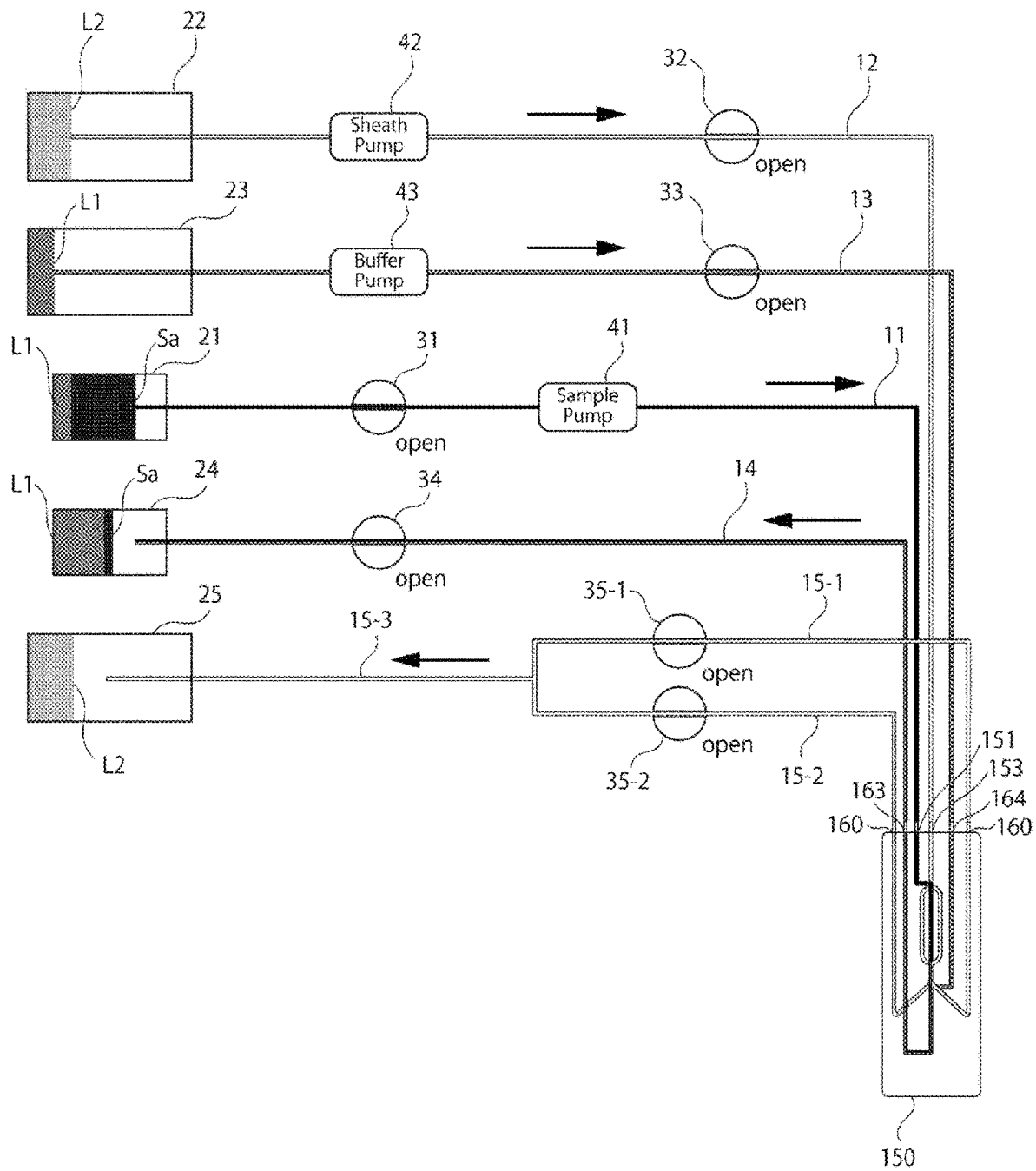
FIG. 11 is a schematic diagram for illustrating a state in which a microparticle sort step is performed after the priming method of the present technology is performed.

After performing the priming method of the present technology, the microparticle is sorted using the microparticle sorting microchip. FIG. 11 illustrates a state in which a microparticle sort step is performed after the priming method of the present technology is performed.

The microparticle sort step may include the flow step, the determination step, and the recovery step described in (2) described above.

In the following, states of the valve and the pump for performing the microparticle sort step are described.

After the first priming step and the second priming step described in (3-2) and (3-3) described above, respectively, are completed, a microparticle-containing sample liquid Sa (for example, microparticle suspension) is introduced into the container 21. The introduction may be performed aseptically, for example. Then, the valve 31 is opened, and the pump 41 is driven to deliver the sample liquid Sa from the container 21 to the sample liquid flow path 152. The first liquid L1 in the sample liquid flow path 152 is replaced with the sample liquid. Then, the sample liquid flows through the sample liquid flow path 152 and further flows through the joined flow path 155. Then, on the microparticle in the sample liquid, the microparticle sorting operation as described in (2) described above may be performed. In the microparticle sorting operation, the recovery target particle and the first liquid L1 flow through the microparticle recovery flow path 159.

At the microparticle sort step, all the valves may be opened as illustrated in FIG. 10. Moreover, the pumps 42 and 43 continue supplying the first liquid L1 (buffer liquid) and the second liquid L2 (sheath liquid) into the microparticle sorting microchip, respectively.

(3-5) First Liquid and Second Liquid

The first liquid and the second liquid used at the first priming step may be selected by one skilled in the art depending on factors such as a type of the microparticle and/or physical characteristics required for flowing in the flow path, for example.

In a preferred embodiment of the present technology, the first liquid is a buffer solution. In this embodiment, the microparticles may be, for example, biological particles, and especially, cells or cell aggregations. Since the first liquid is the buffer solution, a cell membrane of the cell may be maintained, for example. A type of the buffer solution may be selected depending on the type of the microparticles (especially, the cells). The buffer solution preferably includes an electrolyte, and more preferably includes an electrolyte for regulating a plasma osmotic pressure. Examples of the electrolytes may include, for example, sodium and/or potassium. Specific examples of the buffer solution including the electrolyte may include phosphate buffered saline (PBS).

In a preferred embodiment of the present technology, the first liquid includes a protein, and preferably includes a protein that regulates a colloidal osmotic pressure. Examples of the protein may include albumin, for example. Albumin may be human-derived albumin, recombinant human serum albumin, or bovine serum albumin. More specific examples of the first liquid including the protein may include, but are not limited to, serum or plasma. By performing the priming of the flow path by the first liquid including the protein, non-specific adsorption of the microparticle (especially, the cell) to the inner surface of the flow path or the inner surface of the container may be prevented. Furthermore, the priming is also beneficial for the protection of the cell membrane.

In an especially preferred embodiment of the present technology, the first liquid is a buffer solution including a protein (especially, a protein that regulates the colloidal osmotic pressure). Especially preferably, the first liquid is the buffer solution including albumin.

It is especially preferable to use the buffer solution including the protein as the first liquid in order to prevent the non-specific adsorption of the microparticle (especially, the cell) to the inner surface of the flow path or the inner surface of the container.

Furthermore, by using the buffer solution including the protein as the first liquid, it is possible to prevent deterioration in quality of the microparticle (especially, the cell) sorted into the recovery container, and to suppress an increase in a proportion of dead cells, for example. For example, the container into which the recovery target particle is recovered may be rinsed with, for example, the buffer solution including the protein in order to prevent the non-specific adsorption of the cell on the container wall surface. In a case where there is no rinse, the percentage of the dead cells in the cells recovered into the container may increase over time after the recovery. For example, when centrifugation is performed to collect the cells after the recovery, the percentage of the dead cells further increases. In contrast, by using the buffer solution including the protein as the first liquid, it is possible to prevent the increase in the percentage of the dead cells without rinsing the recovery container.

The first liquid may further include a medium or a medium component. Examples of the medium components may include carbohydrates, amino acids, and vitamins, for example.

Examples of the carbohydrates may include glucose and sucrose. The carbohydrates are useful for supplying energy to the cells.

Examples of the amino acids may include essential amino acids and non-essential amino acids. The first liquid preferably includes the essential amino acids as the amino acids, and especially includes glutamine. The amino acids are useful for protein synthesis of the cells, especially for protein synthesis for proliferation.

Examples of the vitamins may include vitamins A, B, C, D, and E. The first liquid may preferably include one or a combination of two or more of vitamins B, A, and E. The vitamins are useful for cell proliferation.

The first liquid preferably does not include phenol red.

The first liquid may further include a nonionic surfactant. The nonionic surfactant may be, for example, a nonionic surfactant used for cell stabilization, and especially, a nonionic surfactant used for cell membrane protection. Examples of such nonionic surfactants may include poloxamers, and more specifically, Pluronic F68.

An example of the first liquid is a buffer solution including plasma or serum, and especially, a culture buffer solution including plasma. A content ratio of the plasma or serum is, for example, 0.1 w/v % to 1.5 w/v %, and more especially 0.2 w/v % to 1.0 w/v %.

Another example of the first liquid is PBS including serum albumin, and especially PBS including bovine serum albumin or human serum albumin. A content ratio of the serum albumin is, for example, 0.1 w/v % to 1.5 w/v %, and more especially 0.2 w/v % to 1.0 w/v %.

Yet another example of the first liquid is PBS including serum albumin and a nonionic surfactant, especially PBS including bovine serum albumin or human serum albumin and a nonionic surfactant. A content ratio of the serum albumin is, for example, 0.1 w/v % to 1.5 w/v %, and more especially 0.2 w/v % to 1.0 w/v %.

An example of the first liquid is a buffer solution including plasma or serum, and especially, a culture buffer solution including plasma. A content ratio of the plasma or serum is, for example, 0.1 w/v % to 1.5 w/v %, and more especially 0.2 w/v % to 1.0 w/v %.

The second liquid may be, for example, a sheath liquid. The sheath liquid may be appropriately selected by one skilled in the art out of the liquids used as the sheath liquid in the art (for example, in the art regarding the flow cytometry).

The second liquid may include, for example, an osmotic pressure regulator and a buffer, and this may more specifically be an aqueous solution of the osmotic pressure regulator and the buffer.

The osmotic pressure regulator may include one or a combination of two or more selected from a group including organic salts, inorganic salts, and saccharides. Examples of the organic salts may include, for example, propionate (more specifically, sodium propionate, potassium propionate, and ammonium propionate), oxalate, and acetate. Examples of the inorganic salts may include, for example, sodium chloride, potassium chloride, and lithium chloride. Examples of the saccharides include, for example, sorbitol, glucose, and mannitol. The osmotic pressure regulator may include, for example, inorganic salts, more specifically sodium chloride, potassium chloride, or a combination thereof.

The buffer may include one or a combination of two or more selected from the group including, for example, phosphate and a Good's buffer. Examples of the phosphate may include disodium hydrogen phosphate, sodium dihydrogen phosphate, and potassium dihydrogen phosphate. Examples of the Good's buffer may include a Tris buffer, MES, Bis-Tris, ADA, PIPES, ACES, MOPSO, BES, MOPS, TES, HEPES, DIPSO, TAPSO, POPSO, HEPPSO, EPPS, Tricine, Bicine, and TAPS. The buffer may include, for example, phosphate, and more specifically, one, two, or three selected from disodium hydrogen phosphate, sodium dihydrogen phosphate, and potassium dihydrogen phosphate. For example, the buffer may include a combination of disodium hydrogen phosphate and potassium dihydrogen phosphate.

In addition to the osmotic pressure regulator and buffer, the second liquid may further include one or two or more components selected from anticoagulants, antibacterial agents, surfactants, and organic solvents. As such a component, the second liquid may include, for example, phenoxyethanol and/or sodium fluoride. Furthermore, as the surfactant, the nonionic surfactant described regarding the first liquid above may be used.

The second liquid may be, for example, an aqueous solution including sodium chloride, potassium chloride, disodium hydrogen phosphate, potassium dihydrogen phosphate, phenoxyethanol, and sodium fluoride. FACSFLOW (BD) may be mentioned as an aqueous solution including such a component.

(3-6) Examples of Other Steps

At the priming step of the present technology, the flow rate may be controlled on the basis of an image of the flow path of the microparticle sorting microchip. An example of a step regarding the control of the flow rate based on the image is described below.

(3-6-1) Flow Rate Increasing Step

The first priming step may include a flow rate increasing step of increasing the flow rate of the first liquid.

In a case of allowing a liquid to flow through a flow path in a dry state to fill the flow path with the liquid, bubbles may remain on a wall surface of the flow path. By performing the flow rate increasing step, the bubbles may be removed. For example, the increase in the flow rate causes the bubbles to flow away from the wall surface. Furthermore, the increase in the flow rate increases a pressure in the flow path, and a dissolution speed of the bubbles into the liquid is improved (Henry's law), so that the bubbles may be removed.

The increase in the flow rate at the flow rate increasing step may be performed temporarily. For example, this may be performed from a certain point in time after the first priming step is started to a certain point in time before the first priming step is finished.

The increase in the flow rate at the flow rate increasing step may be performed by, for example, the control unit controlling a pump that controls the flow rate of the first liquid. The control unit may determine whether or not to start the flow rate increasing step and/or whether or not to finish the flow rate increasing step on the basis of, for example, an image obtained by imaging the flow path of the microparticle sorting microchip.

The control unit may perform edge detection based on a contrast of the image, for example, and detect the presence of the bubbles on the basis of a result of the edge detection. In response to the detection of the presence of the bubbles, the control unit may control the pump that controls the flow rate of the first liquid to increase the flow rate of the first liquid.

Furthermore, the control unit may detect that the bubbles are removed on the basis of the result of the edge detection. In response to the detection that the bubbles are removed, the control unit may control the pump that controls the flow rate of the first liquid to reduce the flow rate of the first liquid.

The imaging may be performed, for example, on the entire microparticle sorting microchip by an imaging device, or may be performed so as to sweep a flow path portion of the microparticle sorting microchip.

At the second priming step as well, the flow rate increasing step may be performed in a manner similar to that at the first priming step. That is, the second priming step may include a flow rate increasing step of increasing the flow rate of the second liquid.

(3-6-2) Arrival Detection Step of Liquid at Microparticle Sorting Microchip

The first priming step may include an arrival detection step of detecting that the first liquid arrives at the microparticle sorting microchip.

When the first priming step is started, the pump that controls the flow rate of the first liquid is driven, so that the first liquid is delivered from the container containing the first liquid through a tube to the microparticle sorting microchip. It is preferable that the first liquid arrives at the microparticle sorting microchip in the shortest possible time. Therefore, it is conceivable to deliver the liquid at the highest pressure acceptable for the microparticle sorting chip and/or the tube. In contrast, if the high pressure is continued even after the first liquid arrives at the microparticle sorting microchip, there is a possibility that the microparticle sorting microchip is destroyed. Therefore, the flow rate of the first liquid may be reduced in response to the detection of the arrival of the first liquid at the microparticle sorting microchip.

The detection may be performed, for example, on the basis of an image of the introduction flow path of the microparticle sorting microchip and the connection between the introduction flow path and the tube. The image may be obtained by the imaging device. The control unit may detect the arrival of the first liquid at the microparticle sorting microchip on the basis of the image. In response to the detection of the arrival, the control unit may control the pump that controls the flow rate of the first liquid to reduce the flow rate of the first liquid.

At the second priming step as well, the arrival detection step may be performed in a manner similar to that at the first priming step. That is, the second priming step may include an arrival detection step of detecting that the second liquid arrives at the microparticle sorting microchip. The detection may be performed, for example, on the basis of an image of the sheath liquid inlet of the microparticle sorting microchip and a connection between the same and a sheath liquid supply tube connected to the sheath liquid inlet.

(3-6-3) Droplet Detection Step in Flow Path

The priming method of the present technology may include a droplet detection step of detecting a droplet in the flow path of the microparticle sorting microchip. The droplet detection step may be performed, for example, before the first priming step, or after the first priming step and before the second priming step.

There is a case where, after the sorting processing by a new microparticle sorting microchip is completed, the microparticle sorting microchip is used again. A priming condition suitable in this case (for example, a liquid flow rate, a priming time, a pump pressure and the like) may differ from a priming condition suitable in a case where the new microparticle sorting microchip is used for the first time. By detecting the presence or absence of the droplet in the flow path at the droplet detection step, it is possible to determine whether or not the microparticle sorting microchip is the microchip used for the first time or the used microchip. For example, in a case where the droplet in the flow path is detected, it may be determined that the microchip is the used microchip, and in a case where this is not detected, it may be determined that the microchip is used for the first time. The priming condition may be changed on the basis of the determination result.

The droplet detection may be performed, for example, on the basis of the image of the flow path of the microparticle sorting microchip. The image may be obtained by the imaging device. The control unit may determine the presence of the droplet in the flow path on the basis of the image.

The control unit may perform edge detection based on a contrast of the image, for example, and detect the presence of the droplet on the basis of a result of the edge detection. In response to the detection of the presence of the droplet, the control unit may determine that the droplet is present in the flow path.

2. Second Embodiment (Microparticle Sorting Method)

The present technology also provides a microparticle sorting method including performing the first priming step, the second priming step, and the microparticle sort step described in 1. described above by using the microparticle sorting microchip described in 1. described above. The description of the microparticle sorting microchip and these steps in 1. described above is also applicable to this embodiment.

In the microparticle sorting method of the present technology, the flow path of the microparticle sorting microchip is efficiently primed by the first priming step and the second priming step. Moreover, the priming may prevent non-specific adsorption of the microparticle to the flow path or the recovery container in the microparticle sort step.

3. Third Embodiment (Microparticle Sorting Device)

The present technology also provides a microparticle sorting device that executes the first priming step and the second priming step on the microparticle sorting microchip as described in 1. described above. After these priming steps, the microparticle sorting device may also execute the microparticle sort step as described in 1. described above. The description of the microparticle sorting device, the microparticle sorting microchip, and these steps in 1. described above is also applicable to this embodiment.

For example, the control unit 103 described in 1. described above may control opening and closing of the valve group as described in (3-2) of 1. described above, for example, at the first priming step. After controlling the valve group, the control unit 103 controls the pump group as described in (3-2) of 1. described above, for example, and the priming is performed by the first liquid L1.

For example, the control unit 103 described in 1. described above may control the opening and closing of the valve group as described in (3-3) of 1. described above, for example, at the second priming step. After controlling the valve group, the control unit 103 controls the pump group, for example, as described in (3-3) of 1. described above, and the priming is performed by the second liquid L2.

At the microparticle sort step, the microparticle sorting operation as described in 1. described above may be performed.

Furthermore, the microparticle sorting microchip may be removable from the microparticle sorting device. Since the microparticle sorting microchip is removable from the device, a new microparticle sorting microchip may be used for each sample, thereby preventing contamination between samples.

The microparticle sorting device of the present technology may also include an imaging device that images the flow path of the microparticle sorting microchip. The imaging device may obtain an image used for executing the flow rate increasing step, the arrival detection step, or the droplet detection step described in "(3-6) Examples of other steps" described above. The imaging device may include an imaging element such as a CCD or a CMOS, for example, and a magnifying optical system such as a lens, for example. The configuration of the imaging device may be appropriately selected by one skilled in the art depending on factors such as, for example, the type of the image that should be obtained and/or the size of the flow path.

4. Fourth Embodiment (Program)

The present technology also provides a program for allowing the microparticle sorting device to execute the first priming step and the second priming step on the microparticle sorting microchip as described in 1. described above. The description of the microparticle sorting device, the microparticle sorting microchip, and these steps in 1. described above is also applicable to this embodiment.

The program may be stored in a hard disk provided in the microparticle sorting device 100, or may be recorded on a recording medium such as a microSD memory card, an SD memory card, or a flash memory, for example. The control unit 103 may allow the microparticle sorting device 100 to execute the priming method of the present technology according to the program.

Note that, the present technology may also have a following configuration.

[1] A priming method of a microparticle sorting microchip provided with:
  a sample liquid flow path;
  a sheath liquid flow path that joins the sample liquid flow path at a junction;
  a joined flow path including the junction at one end;
  a microparticle recovery flow path connected to the joined flow path via a connection flow path at the other end of the joined flow path;
  a branching flow path connected to the joined flow path at the other end of the joined flow path; and
  an introduction flow path configured to introduce a liquid into the connection flow path,
  the method provided with:
  a first priming step of supplying a first liquid from the introduction flow path to the connection flow path, and performing priming on the microparticle recovery flow path by the first liquid; and
  a second priming step of allowing a second liquid to flow from the sheath liquid flow path to the joined flow path, and performing priming on the branching flow path by the second liquid.

[2] The priming method according to [1], in which the first liquid is a buffer solution.

[3] The priming method according to [1] or [2], in which the first liquid includes a protein that regulates a colloidal osmotic pressure.

[4] The priming method according to any one of [1] to [3], in which the second priming step is performed while continuing the supply of the first liquid to the connection flow path at the first priming step.

[5] The priming method according to any one of [1] to [4], in which the joined flow path includes a sort discrimination unit used for performing sort discrimination of a microparticle.

[6] The priming method according to any one of [1] to [5], in which, at the first priming step, the joined flow path is primed by the first liquid.

[7] The priming method according to any one of [1] to [6], in which, at the first priming step, a recovery container of a microparticle that flows toward the microparticle recovery flow path is primed by the first liquid.

[8] The priming method according to any one of [1] to [7], in which, at the first priming step, a container into which a sample liquid is introduced is primed by the first liquid.

[9] The priming method according to any one of [1] to [8], in which, at the second priming step, the joined flow path is primed by the second liquid.

[10] The priming method according to any one of [1] to [9], in which, after performing the priming method, a microparticle is sorted using the microparticle sorting microchip.

[11] The priming method according to any one of [1] to [10], in which, after performing the priming method, a sample liquid is introduced into a first liquid supply container for supplying the first liquid to the sample liquid flow path, and thereafter, a microparticle included in the sample liquid is sorted using the microparticle sorting microchip.

[12] The priming method according to [11], in which the sample liquid is aseptically introduced into the first liquid supply container.

[13] The priming method according to any one of [1] to [12], in which the microparticle is a biological particle.

[14] The priming method according to any one of [1] to [13], in which the microparticle is a cell.

[15] A microparticle sorting method in a microparticle sorting microchip provided with:
a sample liquid flow path;
a sheath liquid flow path that joins the sample liquid flow path at a junction;
a joined flow path including the junction at one end;
a microparticle recovery flow path connected to the joined flow path via a connection flow path at the other end of the joined flow path;
a branching flow path connected to the joined flow path at the other end of the joined flow path; and
an introduction flow path configured to introduce a liquid into the connection flow path,
the method provided with:
a first priming step of supplying a first liquid from the introduction flow path to the connection flow path, and performing priming on the microparticle recovery flow path by the first liquid;
a second priming step of allowing a second liquid to flow from the sheath liquid flow path to the joined flow path, and performing priming on the branching flow path by the second liquid; and
a microparticle sort step of sorting a microparticle using the microparticle sorting microchip after the second priming step.

[16] A microparticle sorting device that executes, on a microparticle sorting microchip provided with:
a sample liquid flow path;
a sheath liquid flow path that joins the sample liquid flow path at a junction;
a joined flow path including the junction at one end;
a microparticle recovery flow path connected to the joined flow path via a connection flow path at the other end of the joined flow path;
a branching flow path connected to the joined flow path at the other end of the joined flow path; and
an introduction flow path configured to introduce a liquid into the connection flow path,
a first priming step of supplying a first liquid from the introduction flow path to the connection flow path, and performing priming on the microparticle recovery flow path by the first liquid; and
a second priming step of allowing a second liquid to flow from the sheath liquid flow path to the joined flow path, and performing priming on the branching flow path by the second liquid.

[17] A program for allowing a microparticle sorting device to execute,
in a microparticle sorting microchip provided with:
a sample liquid flow path;
a sheath liquid flow path that joins the sample liquid flow path at a junction;
a joined flow path including the junction at one end;
a microparticle recovery flow path connected to the joined flow path via a connection flow path at the other end of the joined flow path;
a branching flow path connected to the joined flow path at the other end of the joined flow path; and
an introduction flow path configured to introduce a liquid to the connection flow path,
a first priming step of supplying a first liquid from the introduction flow path to the connection flow path, and performing priming on the microparticle recovery flow path by the first liquid; and
a second priming step of allowing a second liquid to flow from the sheath liquid flow path to the joined flow path, and performing priming on the branching flow path by the second liquid.

REFERENCE SIGNS LIST

100 Microparticle sorting device
150 Microparticle sorting microchip
155 Joined flow path
159 Microparticle recovery flow path
161 Introduction flow path
170 Connection flow path

The invention claimed is:

1. A priming method of a microparticle sorting microchip provided with: a sample liquid flow path; a sheath liquid flow path that joins the sample liquid flow path at a junction; a joined flow path including the junction at one end; a microparticle recovery flow path connected to the joined flow path via a connection flow path at the opposite end of the joined flow path; a branching flow path connected to the joined flow path at the opposite end of the joined flow path; and an introduction flow path configured to introduce a first liquid into the connection flow path, the method comprising: a first priming step of supplying a first liquid from the introduction flow path to the connection flow path, and performing priming on the microparticle recovery flow path by the first liquid; and a second priming step of allowing a second liquid to flow from the sheath liquid flow path to the joined flow path, and performing priming on the branching flow path by the second liquid.

2. The priming method according to claim 1, wherein the first liquid is a buffer solution.

3. The priming method according to claim 1, wherein the first liquid includes a protein that regulates a colloidal osmotic pressure.

4. The priming method according to claim 1, wherein the second priming step is performed while continuing the supply of the first liquid to the connection flow path at the first priming step.

5. The priming method according to claim 1, wherein the joined flow path includes a sort discrimination unit used for performing sort discrimination of a microparticle.

6. The priming method according to claim 1, wherein, at the first priming step, the joined flow path is primed by the first liquid.

7. The priming method according to claim 1, wherein, at the first priming step, a recovery container of a microparticle that flows toward the microparticle recovery flow path is primed by the first liquid.

8. The priming method according to claim 1, wherein, at the first priming step, a container into which a sample liquid is introduced is primed by the first liquid.

9. The priming method according to claim 1, wherein, at the second priming step, the joined flow path is primed by the second liquid.

10. The priming method according to claim 1, wherein, after performing the priming method, a microparticle is sorted using the microparticle sorting microchip.

11. The priming method according to claim 1, wherein, after performing the priming method, a sample liquid is introduced into a first liquid supply container for supplying the first liquid to the sample liquid flow path, and thereafter,
a microparticle included in the sample liquid is sorted using the microparticle sorting microchip.

12. The priming method according to claim 11, wherein the sample liquid is aseptically introduced into the first liquid supply container.

13. The priming method according to claim 1, wherein the microparticle is a biological particle.

14. The priming method according to claim 1, wherein the microparticle is a cell.

15. A microparticle sorting method in a microparticle sorting microchip provided with: a sample liquid flow path; a sheath liquid flow path that joins the sample liquid flow path at a junction; a joined flow path including the junction at one end; a microparticle recovery flow path connected to the joined flow path via a connection flow path at the opposite end of the joined flow path; a branching flow path connected to the joined flow path at the opposite end of the joined flow path; and an introduction flow path configured to introduce a first liquid into the connection flow path, the method comprising: a first priming step of supplying a first liquid from the introduction flow path to the connection flow path, and performing priming on the microparticle recovery flow path by the first liquid; a second priming step of allowing a second liquid to flow from the sheath liquid flow path to the joined flow path, and performing priming on the branching flow path by the second liquid; and a microparticle sort step of sorting a microparticle using the microparticle sorting microchip after the second priming step.

* * * * *